(12) United States Patent
Gavala et al.

(10) Patent No.: US 9,877,738 B2
(45) Date of Patent: Jan. 30, 2018

(54) OSCILLATING LITHOTRIPTER

(71) Applicant: Gyrus ACMI, Inc., Southborough, MA (US)

(72) Inventors: Artemie G. Gavala, Sutton, MA (US); Lawrence J. St. George, Sudbury, MA (US); Tie Hu, Marlborough, MA (US)

(73) Assignee: Gyrus ACMI, Inc., Southborough, MA (US)

( * ) Notice: Subject to any disclaimer, the term of this patent is extended or adjusted under 35 U.S.C. 154(b) by 531 days.

(21) Appl. No.: 14/274,216

(22) Filed: May 9, 2014

(65) Prior Publication Data

US 2014/0336665 A1 Nov. 13, 2014

Related U.S. Application Data

(60) Provisional application No. 61/821,518, filed on May 9, 2013.

(51) Int. Cl.
*A61B 17/22* (2006.01)
*A61B 17/00* (2006.01)
*A61B 17/32* (2006.01)

(52) U.S. Cl.
CPC .......... *A61B 17/22012* (2013.01); *A61B 2017/00473* (2013.01); *A61B 2017/22014* (2013.01);
(Continued)

(58) Field of Classification Search
CPC .......... A61B 2017/22014; A61B 2017/00026; A61B 2017/00411; A61B 17/22012; A61B 17/12022; A61B 17/12118; A61B 17/32002; A61B 1/307; A61B 5/0438; A61B 8/12; A61H 1/00; A61H 2023/0209;
(Continued)

(56) References Cited

U.S. PATENT DOCUMENTS 3,823,717 A 7/1974 Pohlman et al.
5,134,349 A 7/1992 Kruse
(Continued)

FOREIGN PATENT DOCUMENTS

CN 101380244 A 3/2009
GB 2176113 A1 12/1986
(Continued)

*Primary Examiner* — Jonathan Miles
*Assistant Examiner* — Mohamed Gabr
(74) *Attorney, Agent, or Firm* — Gerald P. Kazanjian; Pegah Karimi

(57) ABSTRACT

A lithotripter is provided for fragmenting a stone inside a patient's body. In one form, the lithotripter includes a motor having at least two modes of operation and is configured to produce first and second waveforms. A wave guide shaft is configured to transmit the first and second waveforms to the stone. In one form, at least one of the first and second waveforms is provided to the stone at a frequency that is about equal to a natural frequency of the stone. In a variation, the lithotripter may include an ultrasonic driver configured to produce an ultrasonic frequency waveform and a sonic driver configured to produce a sonic frequency waveform. The sonic driver is mechanically coupled to the ultrasonic driver. The ultrasonic driver and the sonic driver may be disposed within a driver housing. In another variation, the lithotripter may include a brushless DC motor.

28 Claims, 18 Drawing Sheets

(52) U.S. Cl.
CPC ............. *A61B 2017/22079* (2013.01); *A61B 2017/32008* (2013.01); *A61B 2017/320072* (2013.01)

(58) Field of Classification Search
CPC ... A61H 31/005; A61H 31/006; A61M 25/00; A61M 25/01; G10K 15/06; H02P 6/08; H02P 7/182
USPC .......................................................... 606/128
See application file for complete search history.

(56) References Cited

U.S. PATENT DOCUMENTS

| | | | |
|---|---|---|---|
| 2003/0003418 A1* | 1/2003 | Kumabe | .................. A61C 1/07 433/119 |
| 2003/0045887 A1* | 3/2003 | Sakurai | .......... A61B 17/320092 606/128 |
| 2006/0036168 A1 | 2/2006 | Liang | |
| 2008/0188864 A1 | 8/2008 | Ducharme | |
| 2008/0287793 A1 | 11/2008 | Hoffmann | |
| 2010/0286791 A1 | 11/2010 | Goldsmith | |
| 2011/0251623 A1* | 10/2011 | Ding | ................ A61B 17/22012 606/128 |
| 2012/0302820 A1 | 11/2012 | Carmeli | |

FOREIGN PATENT DOCUMENTS

| | | |
|---|---|---|
| JP | 62292154 A | 12/1987 |
| JP | 04-022350 | 1/1992 |
| JP | 2011025060 A | 2/2011 |
| WO | 2004/060141 A3 | 7/2004 |
| WO | 2004060141 A2 | 7/2004 |

* cited by examiner

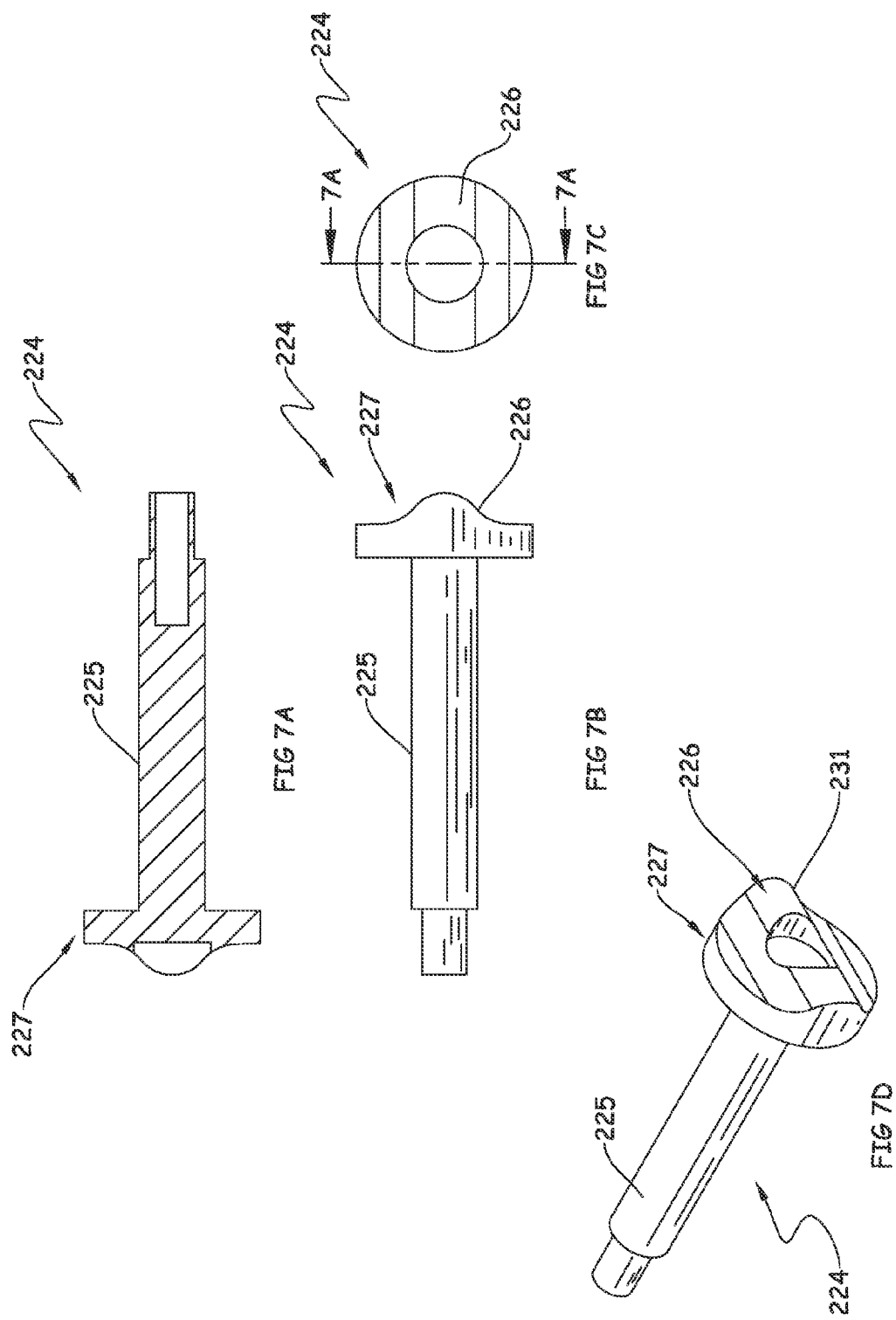

OSCILLATING LITHOTRIPTER

RELATED APPLICATION

The present application claims the benefit of U.S. Provisional Patent Application No. 61/821,518, filed on May 9, 2013, the entire contents of which are incorporated herein by reference.

FIELD

The present disclosure relates to a medical device, and more particularly to a lithotripter for fragmenting stones in a patient's body.

BACKGROUND

The statements in this section merely provide background information related to the present disclosure and may or may not constitute prior art.

Lithotripsy is a common method for fragmenting stones, or calculi, in the urinary tract, kidneys, and/or bladder. Most lithotripsy devices use ultrasound, laser, or pneumatic energy sources to fragment such stones. Typically, the lithotripter includes a shaft connected to an electrically controlled driver or a pneumatic actuator. The shaft is inserted into the patient's anatomy to a location near the stone, and a waveform is sent through the shaft to impact the stone with the shaft to create a jackhammer or drilling effect on the stone, thus fragmenting the stone into smaller elements that are easier to remove. The stone fragments are then removed by irrigation and/or baskets.

Among the literature that can pertain to this technology include the following patent documents and published patent applications: US 2006/0036168; US 2008/0287793; US 2010/0286791; US 2011/0251623; US2008/0188864; U.S. Pat. No. 7,229,455; U.S. Pat. No. 6,575,956; U.S. Pat. No. 4,721,107; U.S. Pat. No. 5,628,743; and U.S. Pat. No. 8,226,629, all incorporated by reference for all purposes.

Current lithotripsy devices may be expensive, complicated, and/or less effective at fragmenting stones than desired. For example, certain lithotripsy methods may include the use of a first driver to provide a first waveform to the stone through a first shaft and a second driver to provide another waveform to the stone through a second shaft that is concentrically mounted around the first shaft. Though insertion of a lithotripter through the patient's urethra and ureter may be desired, such a device requires percutaneous access to the stone due to the large combined shaft size. In another example, a single driver is used to provide a waveform to the stone, however, the single waveform may not fragment the stone as well as desired.

Accordingly, there exists a need for more effective, simpler, smaller, and/or less expensive lithotripsy devices.

SUMMARY

The present disclosure provides an improved lithotripter having at least two modes of operation for providing a waveform to a stone in a patient's anatomy, and a shaft to carry the waveform to the stone.

In one aspect, which may be combined with or separate from the other aspects described herein, the present disclosure provides a lithotripter for fragmenting urinary tract stones. The lithotripter includes an ultrasonic driver configured to produce an ultrasonic waveform having an ultrasonic frequency and a sonic driver configured to produce a sonic waveform having a sonic frequency. The sonic driver is mechanically coupled to the ultrasonic driver. The ultrasonic driver and the sonic driver are disposed within a driver housing. A wave guide shaft is provided for transmitting the ultrasonic and sonic waveforms to at least one urinary tract stone. The wave guide shaft is driven by at least one of the ultrasonic driver and the sonic driver.

In another form, which may be combined with or separate from the other forms disclosed herein, a lithotripter for fragmenting urinary tract stones is provided. The lithotripter includes an ultrasonic driver configured to produce an ultrasonic waveform having an ultrasonic frequency and a sonic driver configured to produce a sonic waveform having a sonic frequency. The sonic driver is coupled to the ultrasonic driver. A wave guide shaft is provided for transmitting the ultrasonic and sonic waveforms to at least one urinary tract stone. The wave guide shaft is coupled to at least one of the ultrasonic driver and the sonic driver. The sonic waveform is provided at a frequency that is about equal to a natural frequency of the urinary tract stone.

In yet another form, which may be combined with or separate from the other forms disclosed herein, a method of fragmenting urinary tract stones is provided. The method includes determining a size, determining a type, or determining both a size and type of a urinary tract stone and selecting a magnitude of a sonic frequency for producing a sonic waveform, the magnitude of the sonic frequency being selected based on the size of the urinary tract stone. The method also includes producing the sonic waveform using a sonic driver and producing an ultrasonic waveform having an ultrasonic frequency using an ultrasonic driver. The method further includes transmitting the sonic waveform and the ultrasonic waveform to the urinary tract stone via a wave guide shaft.

In still another form, which may be combined with or separate from the other forms described herein, a lithotripter for fragmenting a stone inside a patient's body is provided. The lithotripter includes a motor having at least two modes of operation. The motor is configured to produce a first waveform and a second waveform. A wave guide shaft is configured to transmit the first and second waveforms to the stone. The motor is configured to provide at least one of the first and second waveforms to the stone at a frequency that is about equal to a natural frequency of the stone.

In still another form, which may be combined with or separate from the other forms described herein, a lithotripter assembly is provided for fragmenting a stone inside a patient's body. The lithotripter includes a brushless DC motor, a mechanical motion converter, and a wave guide shaft. The brushless DC motor is operable to produce a rotational motion. The mechanical motion converter is configured to convert the rotational motion of the brushless DC motor to a linear waveform. The wave guide shaft is configured to transmit the linear waveform to the stone.

Accordingly, pursuant to one aspect of the invention, there is contemplated an apparatus comprising one or more of the following: an ultrasonic driver configured to produce an ultrasonic waveform having an ultrasonic frequency; a sonic driver configured to produce a sonic waveform having a sonic frequency, the sonic driver being mechanically coupled to the ultrasonic driver; a driver housing, the ultrasonic driver and the sonic driver being disposed within the driver housing; and a wave guide shaft for transmitting the ultrasonic and sonic waveforms to at least one urinary tract stone, the wave guide shaft being driven by at least one of the ultrasonic driver and the sonic driver.

Accordingly, pursuant to another aspect of the invention, there is contemplated an apparatus comprising one or more of the following: an ultrasonic driver configured to produce an ultrasonic waveform having an ultrasonic frequency; a sonic driver configured to produce a sonic waveform having a sonic frequency, the sonic driver being coupled to the ultrasonic driver; and a wave guide shaft for transmitting the ultrasonic and sonic waveforms to at least one urinary tract stone, the wave guide shaft being coupled to at least one of the ultrasonic driver and the sonic driver; and wherein the sonic waveform is provided at a frequency that is about equal to a natural frequency of the urinary tract stone.

Accordingly, pursuant to yet another aspect of the invention, there is contemplated a method comprising one or more of the following steps: determining a size, determining a type, or determining both a size and a type of a urinary tract stone; selecting a magnitude of a sonic frequency for producing a sonic waveform, the magnitude of the sonic frequency being selected based on the size of the urinary tract stone; producing the sonic waveform using a sonic driver; producing an ultrasonic waveform having an ultrasonic frequency using an ultrasonic driver; and transmitting the sonic waveform and the ultrasonic waveform to the urinary tract stone via a wave guide shaft.

Accordingly, pursuant to still another aspect of the present invention, there is contemplated an apparatus comprising one or more of the following: a motor having at least two modes of operation, the motor configured to produce a first waveform and a second waveform; and a wave guide shaft configured to transmit the first and second waveforms to the stone; and wherein the motor is configured to provide at least one of the first and second waveforms to the stone at a frequency that is about equal to a natural frequency of the stone.

The invention may be further characterized by one or any combination of the features described herein, such as: the sonic driver is an electromagnetic linear driver; the sonic driver is one of a voice coil motor, a moving coil, a moving magnet, and a dual coil; the ultrasonic driver is a piezoelectric stack; the sonic driver is configured to produce the sonic waveform at a sonic frequency that is about equal to a natural frequency of the urinary tract stone; the ultrasonic driver and the sonic driver are disposed in series within the housing; the ultrasonic driver has a proximal end and a distal end; the sonic driver has a proximal end and a distal end; the proximal end of the ultrasonic driver is disposed adjacent to the distal end of the sonic driver; the sonic driver is adjustable to provide the sonic waveform at various frequencies; the sonic driver is adjustable to provide the sonic waveform at a first frequency, a second frequency, and a third frequency, wherein the first frequency is in the range of about 0.3-16 Hz, the second frequency is in the range of about 16-70 Hz, and the third frequency is in the range of about 70-200 Hz; the ultrasonic driver is configured to provide the ultrasonic waveform at an ultrasonic frequency in the range of about 20-30 kHz; the lithotripter further comprises a closed loop feedback circuit configured to determine a preferred ultrasonic frequency that oscillates at a maximum amplitude; the wave guide shaft is rigid; the wave guide shaft is one of semi-rigid and flexible; the ultrasonic driver is configured to produce the ultrasonic waveform having an ultrasonic waveform amplitude in the range of about 10-50 micrometers; the sonic driver is configured to produce the sonic waveform having a sonic waveform amplitude in the range of about 0.5-2 millimeters; the wave guide shaft has a shaft length that is configured to deliver the ultrasonic waveform at a maximum amplitude of the ultrasonic waveform; the shaft length is provided in an increment of a half ultrasonic wavelength of the ultrasonic waveform; the lithotripter further comprises first and second springs; the first spring is connected to the proximal end of the sonic driver and a proximal end of the driver housing; the second spring is connected to the distal end of the ultrasonic driver and a distal end of the driver housing; either or both of the proximal and distal springs may also be configured to act in place of a linear bearing, axially supporting and guiding the moving driver elements, thusly providing a linear bearing element function while also providing a necessary mechanical spring element function; the lithotripter has portions forming a lumen therethrough for at least one of suctioning and irrigating a urinary tract; the lithotripter further comprises a stone size detector for detecting the size of the at least one urinary tract stone; the stone size detector comprises at least one of an optical detector and an ultrasonic echo detector; the lithotripter is configured to automatically set the sonic driver to provide the sonic waveform at one of the first, second, and third frequencies based on the size of the at least one urinary tract stone; the lithotripter is configured to set the sonic driver to provide the sonic waveform at the first frequency if the at least one urinary tract stone is greater than about 10 millimeters in diameter; the lithotripter is configured to set the sonic driver to provide the sonic waveform at the second frequency if the at least one urinary tract stone is greater than about 2-3 millimeters in diameter and less than or equal to about 10 millimeters in diameter; the lithotripter is configured to set the sonic driver to provide the sonic waveform at the third frequency if the at least one urinary tract stone is less than or equal to about 2-3 millimeters in diameter; the ultrasonic driver and the sonic driver are disposed concentrically; the sonic driver has portions forming a cavity therein, the ultrasonic driver being disposed in the cavity of the sonic driver; the lithotripter further comprises a pulsater configured to gate the ultrasonic waveform; the value of the sonic frequency is provided at about the natural frequency of the urinary tract stone; the method further comprises electronic gating the ultrasonic waveform with a square wave of variable frequency and duty cycle consistent with the first, second and third frequencies described above; the lithotripter assembly further comprises a controller configured to operate the brushless DC motor in at least a first mode of operation and a second mode of operation; the first mode of operation is an over-shoot impulse mode and the second mode of operation is a high speed rotational mode; the brushless DC motor has a rotor; in the over-shoot impulse mode, an impulse torque is generated by the brushless DC motor by moving the rotor in a partial rotation; in the high speed rotational mode, the brushless DC motor operates the rotor in a continuous rotational motion; in the over-shoot impulse mode, the rotor is moved in at least one step of less than a full rotation of the rotor to generate a torque on the wave guide shaft; in the over-shoot impulse mode, the rotor in moved in a plurality of back-and-forth steps of between about ten and thirty degrees; the controller is a proportional-integral-derivative (PID) controller; the lithotripter assembly further comprises a position feedback sensor configured to determine the position of the rotor; the position feedback sensor is configured to provide rotor position data to the PID controller; the lithotripter assembly further comprises a housing surrounding the brushless DC motor and the mechanical motion converter; the housing is a handle; the wave guide shaft extends from the handle; the mechanical motion converter comprises a coupler having a cam surface contacting one of: the rotor and an extension connected to the rotor.

Further aspects, advantages and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 7A is a cross-sectional view of a probe coupler of the lithotripter of FIG. 5, according to the principles of the present disclosure;

FIG. 7B is a side view of the probe couple of FIG. 7A, in accordance with the principles of the present disclosure;

FIG. 7C is an end view of the probe coupler of FIGS. 7A-7B, according to the principles of the present disclosure;

FIG. 7D is a perspective view of the probe coupler of FIGS. 7A-7C, in accordance with the principles of the present disclosure;

DETAILED DESCRIPTION

The following description is merely exemplary in nature and is not intended to limit the present disclosure, application, or uses. The present invention relates to a lithotripter for fragmenting stones.

A lithotripter for fragmenting a stone inside a patient's body is provided. The lithotripter may include a motor (which may have multiple drivers) having at least two modes of operation. The motor is configured to produce a first waveform and a second waveform. A wave guide shaft is configured to transmit the first and second waveforms to the stone. In some forms, at least one of the first and second waveforms is provided to the stone at a frequency that is about equal to a natural frequency of the stone.

Figure 1A:
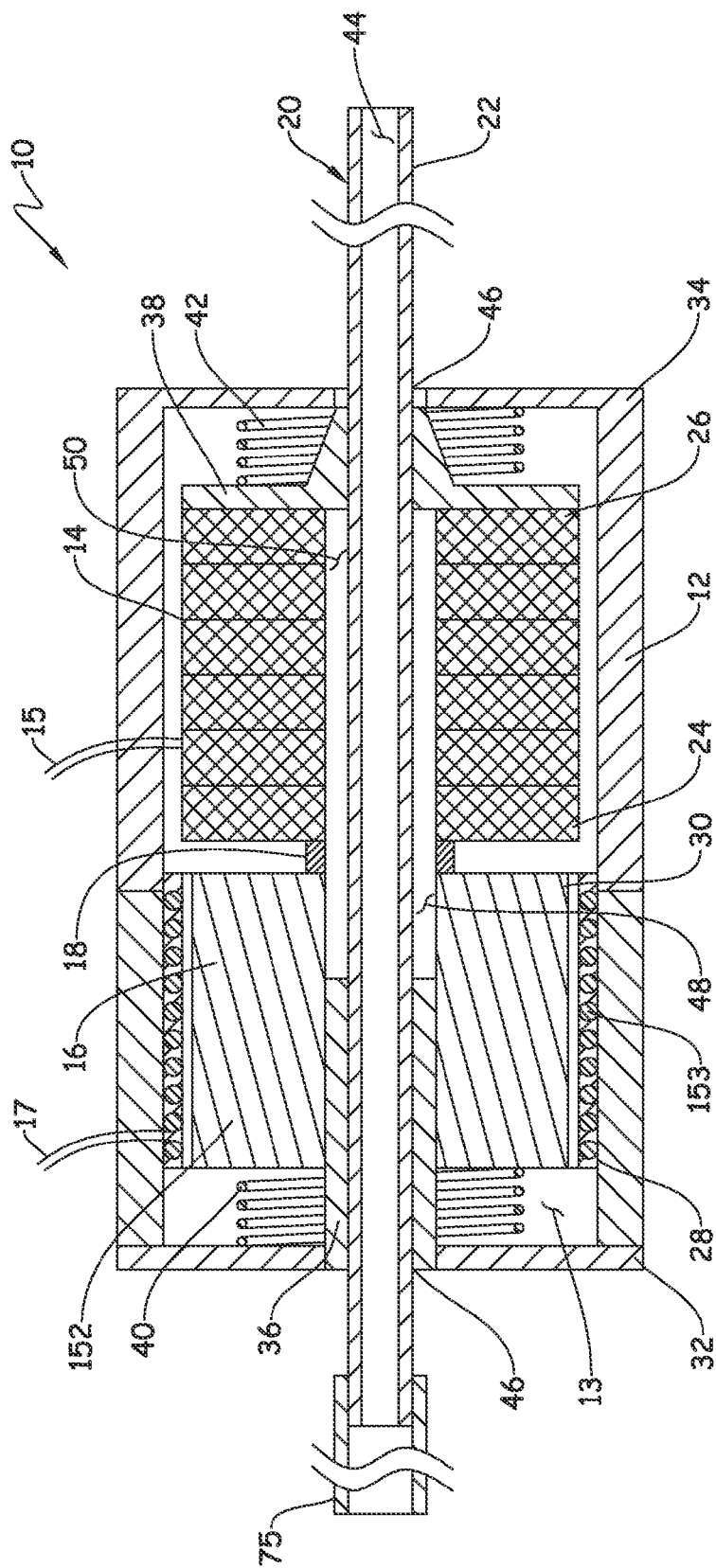
FIG. 1A is a side cross-sectional view of a lithotripter for fragmenting stones, in accordance with the principles of the present disclosure.

With reference to the figures, wherein like numerals indicate like components, and specifically with reference to FIG. 1A, an example of a lithotripter in accordance with the principles of the present disclosure is illustrated and generally designated at 10. The lithotripter 10 may be used for fragmenting stones in a patient's anatomy, such as in a patient's urinary tract, bladder, or kidneys.

The lithotripter 10 includes a driver housing 12 surrounding an ultrasonic driver 14 and a sonic driver 16. Thus, the ultrasonic driver 14 and the sonic driver 16 are disposed in a cavity 13 of the driver housing 12. The ultrasonic driver 14 is configured to produce an ultrasonic waveform having an ultrasonic frequency, and the sonic driver 16 is configured to produce a sonic waveform having a sonic frequency. Lead wires 15 extend from the ultrasonic driver 14, and lead wires 17 extend from the sonic driver 16, so that the ultrasonic driver 14 and/or the sonic driver 16 may be excited by an electrical source (not shown). The sonic driver 16 is mechanically coupled to the ultrasonic driver 14, for example, by way of a connector 18. The connector 18 provides a rigid connection between the ultrasonic and sonic drivers 14, 16. Herein the sonic driver 16 is comprised of the coil 153 and the magnet 152. The magnet 152 is connected to the ultrasonic driver 14 by the connector 18.

A wave guide shaft 20 is provided for transmitting the ultrasonic and sonic waveforms to at least one stone, such as a urinary tract stone. For example, the wave guide shaft 20 may be partially inserted into the patient through the patient's urethra or percutaneously by way of an incision through the patient's skin, by way of example. One or more waveforms may be delivered to the stone by way of the end 22 of the wave guide shaft 20. The wave guide shaft 20 is driven by at least one of the ultrasonic driver 14 and the sonic driver 16, in this embodiment.

In the present example, the ultrasonic driver 14 and the sonic driver 16 are disposed in series within the driver housing 12. More specifically, the ultrasonic driver 14 has a proximal end 24 and a distal end 26, and the sonic driver 16 has a proximal end 28 and a distal end 30. The proximal end 24 of the ultrasonic driver 14 is disposed adjacent to the distal end 30 of the sonic driver 16. The connector 18 contacts and connects the distal end 30 of the sonic driver 30 and the proximal end 24 of the ultrasonic driver 14. Thus, the sonic driver 16 is disposed adjacent to a proximal end 32 of the driver housing 12, and the ultrasonic driver 14 is disposed adjacent to a distal end 34 of the driver housing 12.

The sonic driver 16 is coupled to the wave guide shaft 20 via a linear bearing 36, and the ultrasonic driver 14 is coupled to the wave guide shaft 20 with a connector 38, and therefore, the wave guide shaft 20 also couples the sonic driver 16 and the ultrasonic driver 14 together. It is contemplated that the linear bearing 36 may be made of plastic or other lightweight materials. A first spring 40 is connected to the proximal end 28 of the sonic driver 16 and the proximal end 32 of the driver housing 12. A second spring 42 is connected to the distal end 26 of the ultrasonic driver 14 and the distal end 34 of the driver housing 12.

Figure 1B:
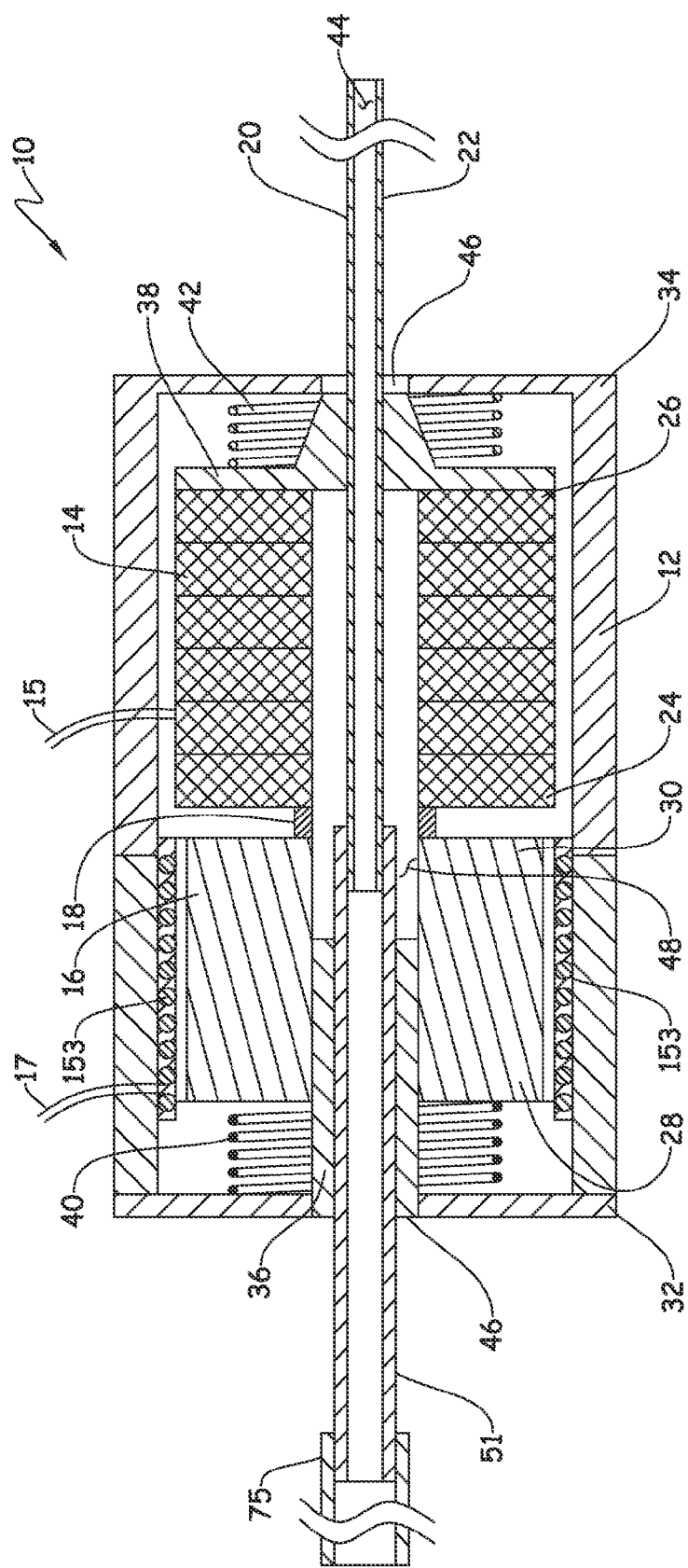
FIG. 1B is a side cross-sectional view of an alternative embodiment of the lithotripter of FIG. 1A, in accordance with the principles of the present disclosure.

The lithotripter 10 has portions forming a lumen or channel therethrough for at least one of suctioning and irrigating a urinary tract. For example, the wave guide shaft 20 has a lumen 44 formed through the center of the wave guide shaft 20 and extending along the length of the wave guide shaft 20. In addition, the housing 12 has openings 46 formed through both the proximal and distal ends 32, 34 of the housing 12, the sonic driver 16 has a channel 48 formed through the center of the sonic driver 16, and the ultrasonic driver 14 has a channel 50 formed through the center of the ultrasonic driver 14. Accordingly, the wave guide shaft 12 extends through the housing 12 and the ultrasonic and sonic drivers 14, 16. The wave guide shaft 20 may be rigid, semi-rigid, or flexible. Alternatively, rather than continuing uninterrupted through the entire assembly, the waveguide shaft may terminate proximally at or within the distal end 38 of the ultrasonic driver 14 and, as an integral element of the ultrasonic driver, the central lumen 44 may continue therethrough and terminate immediately after exiting the proximal end 24 of the ultrasonic driver, as illustrated in FIG. 1B. The central lumen 44 may continue on through the center of the sonic driver 16 as an attached tubular addendum to the central lumen at the proximal end 24 of the ultrasonic driver and terminate after exiting the proximal end of the housing 32 where it may connect to suction tubing for the purposes of removing waste procedural fluids and stone fragments. Tubular addendum 51 of the central lumen 51 originating with the wave guide shaft 20 and continuing through the ultrasonic driver 14 may be comprised of an alternate material, such as plastic. The connection between tubular addendum 51 of the central lumen and the proximal end 24 of ultrasonic driver 14 may be configured to limit interference with the ultrasonic vibration of ultrasonic driver 14. Other configurations of the central lumen 20 and various connection methods of central lumen components may be utilized to minimize dampening effects on the ultrasonic vibration of the ultrasonic driver 14.

The ultrasonic and sonic drivers 14, 16 may take on various forms, without departing from the spirit and scope of the present invention. For example, the sonic driver 16 may be an electromagnetic linear driver. By way of further example, the sonic driver 16 may be a voice coil motor, a moving coil, a moving magnet, or a dual coil. The ultrasonic driver 14 may have a piezoelectric stack. In the exemplary lithotripter configuration presented in FIG. 1, the proximal and distal springs are essential participating elements of the sonic driver's operation, as is the mass of the ultrasonic driver, and will directly affect its operational characteristics. Low friction is an essential element of the sonic driver's efficient operation as the amount of friction opposing the free movement of the sonic driver and by way of connection the ultrasonic driver, will determine the spring force required in the proximal and distal springs to properly control and restore the position of the sonic driver during operation, the power required to drive the sonic motor effectively, and potentially the waste heat energy delivered into the lithotripter assembly and possibly the user's hand.

In some forms, the sonic driver 16 is configured to produce the sonic waveform at a frequency that oscillates at a natural frequency, or resonance frequency, of the targeted stone. For example, the sonic driver 16 may be configured to produce the sonic waveform at a sonic frequency that is about equal to a natural frequency, or resonance frequency, of the targeted stone.

The sonic driver 16 may be adjustable to provide the sonic waveform at various frequencies. For example, the sonic driver 16 may be adjustable to provide the sonic waveform at a first frequency, a second frequency, and a third frequency. The first frequency may be in the range of about 0.3-16 Hz, in the range of about 0.5-8 Hz, or in the range of about 10-16 Hz, by way of example. The second frequency may be in the range of about 16-70 Hz, or in the range of about 40-70 Hz, by way of example. The third frequency may be in the range of about 70-200 Hz, or in the range of about 80-170 Hz, by way of example. The ultrasonic driver 14 may be configured to provide the ultrasonic waveform at an ultrasonic frequency in the range of about 20-30 kHz.

Regarding displacement of the waveforms, the ultrasonic driver 14 may be configured to produce a waveform of about 20 μm, or about 10-50 μm. The sonic driver may be configured to produce a waveform of about 0.5-2 mm, which may be varied by the user. For example, in the first frequency, the sonic driver 16 may be configured to produce a first waveform magnitude of about 1-2 mm; in the second frequency, the sonic driver 16 may be configured to produce a second waveform magnitude of about 0.5-1 mm; and in the third frequency, the sonic driver 16 may be configured to produce a third waveform magnitude of about 0.5 mm.

It is contemplated that the sonic waveform's frequency and/or magnitude may be selected based on the size of the targeted stone. For example, the first frequency and waveform magnitude may be selected for larger stones having a size of about 10-15 mm; the second frequency and waveform magnitude may be selected for medium sized stones having a size of about 3-10 mm; and the third frequency and waveform magnitude may be selected for smaller stones having a size of about 1-3 mm. Though three examples are given, the sonic driver 16 may be configured to provide any number of selectable frequencies and magnitudes.

In some variations, the lithotripter 10 could include one or more selectors to select between the various modes of the sonic driver 16. For example, the selector(s) could be configured to allow the user to select the first, second, or third frequency and/or the first, second, or third waveform magnitude. The selector could include one or more buttons, and/or a slider for fine tuning the selections. For example, the selector could include a first button for selecting the first frequency range and the first waveform magnitude range, and the first ranges could be further chosen with the use of a slider; likewise, the selector could include a second button for selecting the second frequency range and the second waveform magnitude range, and the second ranges could be further chosen with the use of the same slider or a different slider than the slider used for the first ranges; likewise, the selector could include a third button for selecting the third frequency range and the third waveform magnitude range, and the third ranges could be further chosen with the use of the same slider or a different slider than the slider used for the first and/or second ranges.

The lithotripter 10 may further include a stone size, mass, or density detector for detecting the size of a stone. For example, the stone size, mass, or density detector could include an optical detector and/or an ultrasonic echo detector, the lithotripter being configured to automatically set the sonic driver to provide the sonic waveform at one of the first, second, and third frequencies based on the size, mass, or density of stone. The lithotripter 10 may be configured to set the sonic driver 16 to provide the sonic waveform at the first frequency if the target urinary tract stone is greater than about 10 millimeters in diameter; the lithotripter 10 could be configured to set the sonic driver 16 to provide the sonic waveform at the second frequency if the target urinary tract stone is greater than about 2-5 millimeters in diameter and less than or equal to about 10 millimeters in diameter; and the lithotripter 10 could be configured to set the sonic driver 16 to provide the sonic waveform at the third frequency if the target urinary tract stone is less than or equal to about 2-5 millimeters in diameter, by way of example.

The wave guide shaft 20 has a shaft length that is configured to deliver the ultrasonic waveform at a maximum amplitude of the ultrasonic waveform. For example, the shaft length may be provided in an increment of a half ultrasonic wavelength of the ultrasonic waveform, such that the displacement is at the highpoint of the waveform at the distal end 22 of the wave guide shaft 20. The maximum amplitude of the ultrasonic waveform may be the amplitude that most optimally results in stone destruction.

Figure 2:
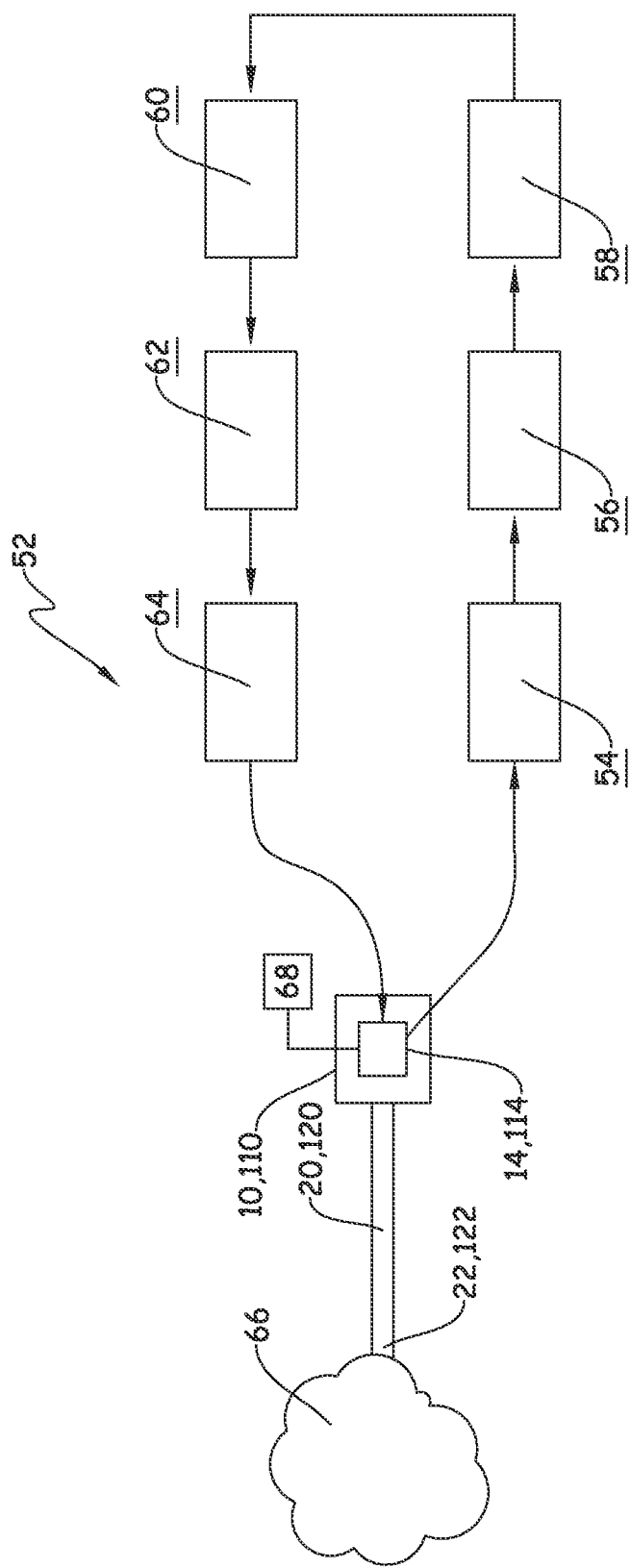
FIG. 2 is a block diagram of a closed loop feedback circuit for use with the lithotripter of FIG. 1 or FIG. 3, according to the principles of the present disclosure.

Referring now to FIG. 2, the lithotripter 10 could include a closed loop feedback circuit 52 configured to determine a preferred ultrasonic frequency that oscillates at a maximum amplitude, producing an anti-node or loop at the distal end 22 of the waveguide shaft 12. For example, the voltage generated by the compression and distension of the piezoelectric element of the ultrasonic driver 14 is captured and amplified by an amplifier (AMP) 54. The analog signal from the amplifier (AMP) 54 is passed to an analog to digital (A/D) converter 56 and converted into a 12-16 bit digital signal. This digital signal is passed to a digital comparator (COMP) 58 where it is compared to an incrementing or decrementing reference generated by a microcontroller. The digital value is adjusted relative to the reference and the previously read value and passed to a digital to analog (D/A) converter 60. The analog signal generated by the digital to analog converter (D/A) 60 drives a voltage controlled oscillator (VCO) 62, which increases or decreases the frequency accordingly. The output of the voltage controlled oscillator (VCO) 62 is amplified by a linear amplifier (AMP) 64 that drives the piezoelectric stack of the ultrasonic driver 14. This way the loop is closed. Once the maximum value is detected by the COMP 58 and the embedded algorithm, the frequency of the ultrasonic driver 14 will be set at its optimum value, for maximum amplitude, which will be delivered to the stone 66 via the distal end 22 of the wave guide shaft 20.

The lithotripter 10 may also include a pulsator 68 configured to gate the ultrasonic waveform. Thus, the ultrasonic driver 14 can be excited with a continuous signal of about 20-30 KHz or with a gated (interrupted) signal of about 20-30 KHz. The gating waveform is a square waveform with variable frequency (0.3-200 Hz) and duty cycle. In some embodiments, the duty cycle is about 80% on, 20% off. In some embodiments, the duty cycle is 50% on, 50% off. It is contemplated that the duty cycle may be in the range of 85-50% on, 15-50% off. This allows the application of pulsating ultrasonic energy at a selected frequency and on/off duration. The frequency and duty cycle of the gating signal can be user selectable. It is contemplated that the pulsating ultrasonic frequency may be in phase with the gating signal.

The lithotripter 10 could have various modes of operation. For example, the lithotripter 10 could be operated in an ultrasonic only mode, such that continuous ultrasonic energy alone is transmitted to the targeted stone 66. The lithotripter 10 could be operated in a gated ultrasonic mode, such that the ultrasonic energy is gated with a square wave signal with variable duty cycle and frequency of about 0.3-200 Hz (consistent with the natural frequency of the targeted stone 66). The lithotripter 10 could be operated in an oscillating ultrasonic mode, wherein the continuous ultrasonic energy is pulsated by the sonic driver 16 with a displacement of about 0.5-2 mm and a frequency about 0.3-200 Hz (consistent with the natural frequency of the stone 66), depending on the selected range. The lithotripter 10 could be operated in an oscillating gated ultrasonic mode, wherein gated ultrasonic energy is pulsated by the sonic driver 16 with a displacement of about 0.5-2 mm and a frequency about 0.3-200 Hz (consistent with the natural frequency of the stone), depending on the selected range. The lithotripter 10 could be operated in a low frequency impact mode, wherein only the low frequency of the sonic driver 16, of about 0.3-200 Hz, is transmitted to the target stone 66 with low amplitude (1-2 mm) and high impact (5-10 lb.) of force producing a jackhammer effect, and the ultrasonic driver 14 is not used.

The ultrasonic and linear driver of the present invention are energized with oscillating frequencies which can be entirely independent or can be synchronized and manipulated in various ways. Energizing the drivers in a synchronized, swept-frequency and gated output method produces very effective results over more continuous and/or single frequency energizing methods. While the ideal ultrasonic resonant frequency is applied, it is interrupted or gated in a continuously variable, repeating way, which may be a low-to-high ramped method in order to provide beneficial lithotripsy results.

In one example, utilizing a frequency at the low end of the ranges to drive a shaft, coupled well with a larger stone (greater than 5 mm, for example) with approximately 1-1.5 kg initial force effectively transfers the sonic and gated ultrasonic energy into the body of the stone and often causes the stone to crack into multiple pieces as the shaft tip is driving through the stone. Smaller size stones are broken up more easily with a mid-range frequency drive for both the oscillating low frequency longitudinal translation drive and the gating of the ultrasonic resonance drive of the lithotripsy shaft and with less force, and the smallest stones may be reduced to an easily evacuated size with frequencies at the higher end of the frequency range with little to no applied force. It is contemplated that sweeping through from the lowest to the highest end of the frequency range that is ideally optimized for the type of stone encountered as well as for the size of the largest fragment, at a sweep rate that allows some duration of time in the vicinity of any one frequency or frequency band to allow the energy of that frequency or frequency band to couple into the stone fragments effectively to cause a more efficient stone breaking effect as the stone or stone fragments experience strong ultrasonic and lower frequency oscillatory energy that would match well with a resonance frequency of the stone material and/or that would exploit weaknesses in the structure of the stone.

As stone fragment size reduces, less force may be necessary to break the stone fragments into smaller pieces. The lithotripsy system may be coupled to an evacuation flow, or suction source, and thus it has been seen that small stone fragments may be vacuumed up by the shaft tip and the ultrasonic energy of the shaft tip may subsequently reduce the size of stone fragments too large to enter the inner diameter of the lithotripsy shaft into sizes that can be easily evacuated. It is contemplated that the distal tip of the lithotripsy shaft may be designed to limit fragment size that may enter through the evacuation flow. Features at the distal end along these lines would help limit the occurrence of stones which may get stuck along the exit pathway due to constrictions or sharp direction changes in the outflow path or if the fragments are too large and may easily settle and interfere with the exit of future fragments.

In some forms, the distal end 22 of wave guide shaft 20 may be placed in contact with the stone 66 and having a jackhammer effect on the stone 66 when one or more of the drivers 14, 16 are activated. However, in other forms, the distal end 22 of the wave guide shaft 20 may be placed adjacent to, but not touching the stone 66. In some forms, the distal end 22 of the wave guide shaft 20 may gently touch the stone 66, but without a jackhammer effect, such that the oscillation breaks up the stone 66. Such a gentle contact may be preferred when the wave guide shaft 20 oscillates at or near the natural frequency of the stone 66.

Figure 3A:
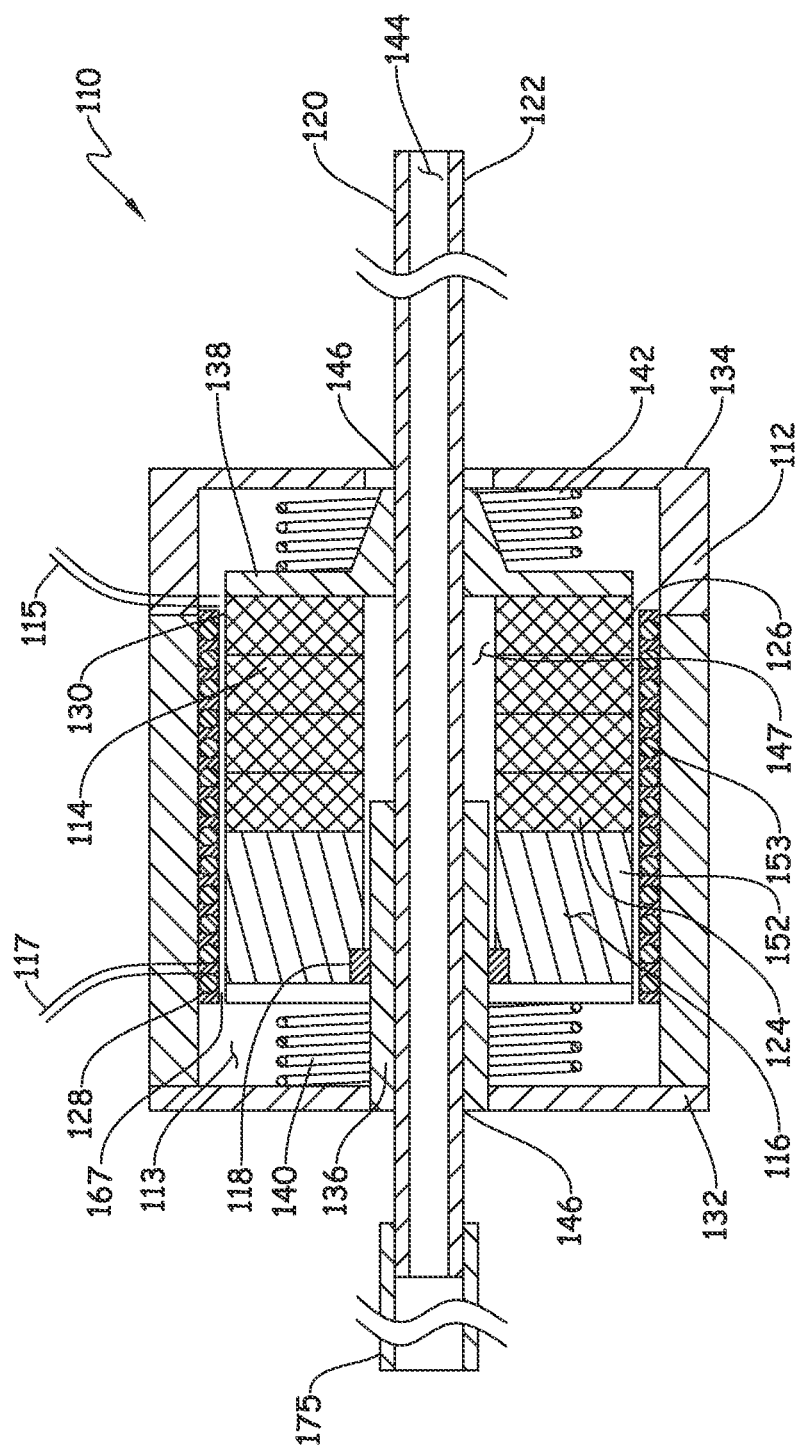
FIG. 3A is a side cross-sectional view of another lithotripter for fragmenting stones, in accordance with the principles of the present disclosure.
Figure 3B:
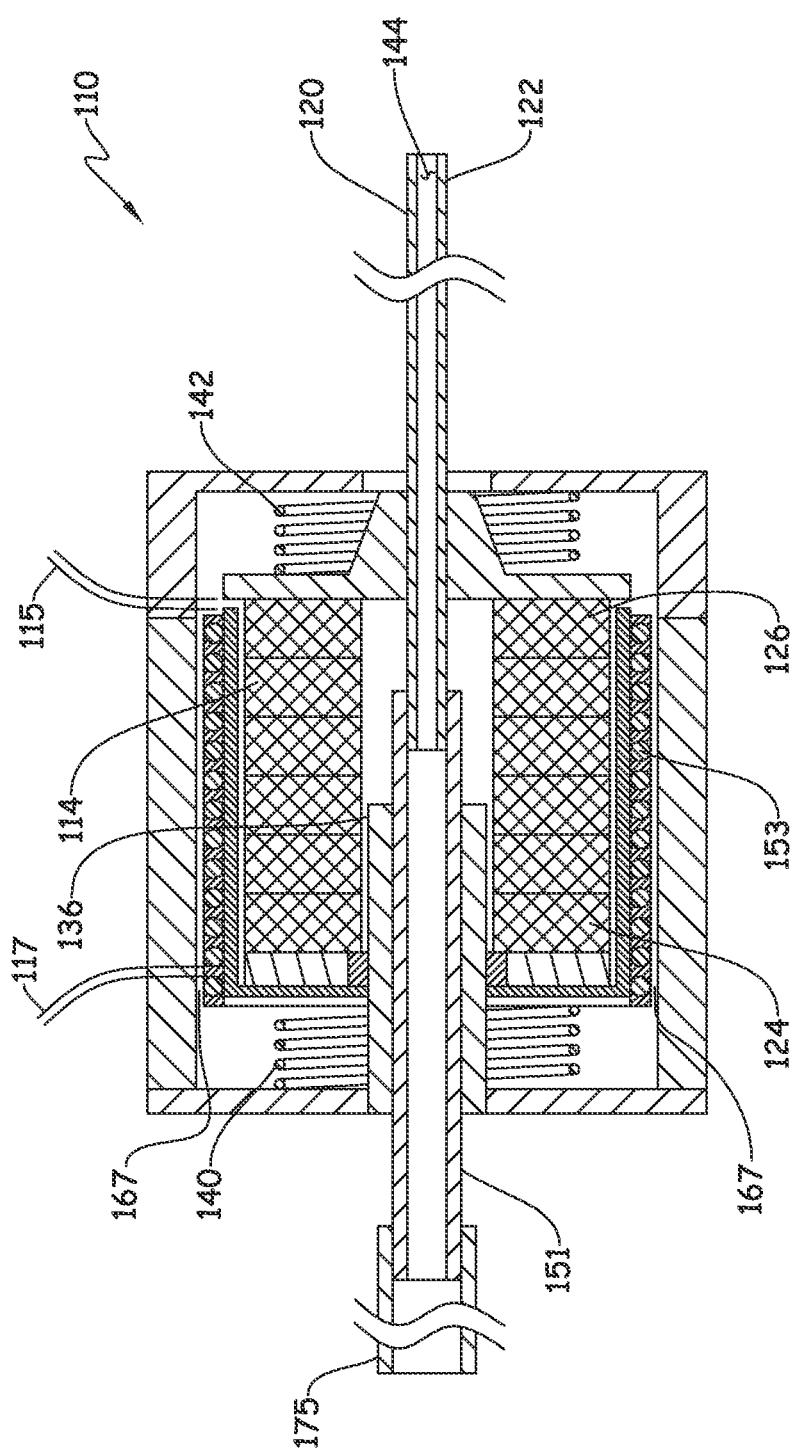
FIG. 3B is a side cross-sectional view of an alternative embodiment of the lithotripter of FIG. 3A, in accordance with the principles of the present disclosure.
Figure 3C:
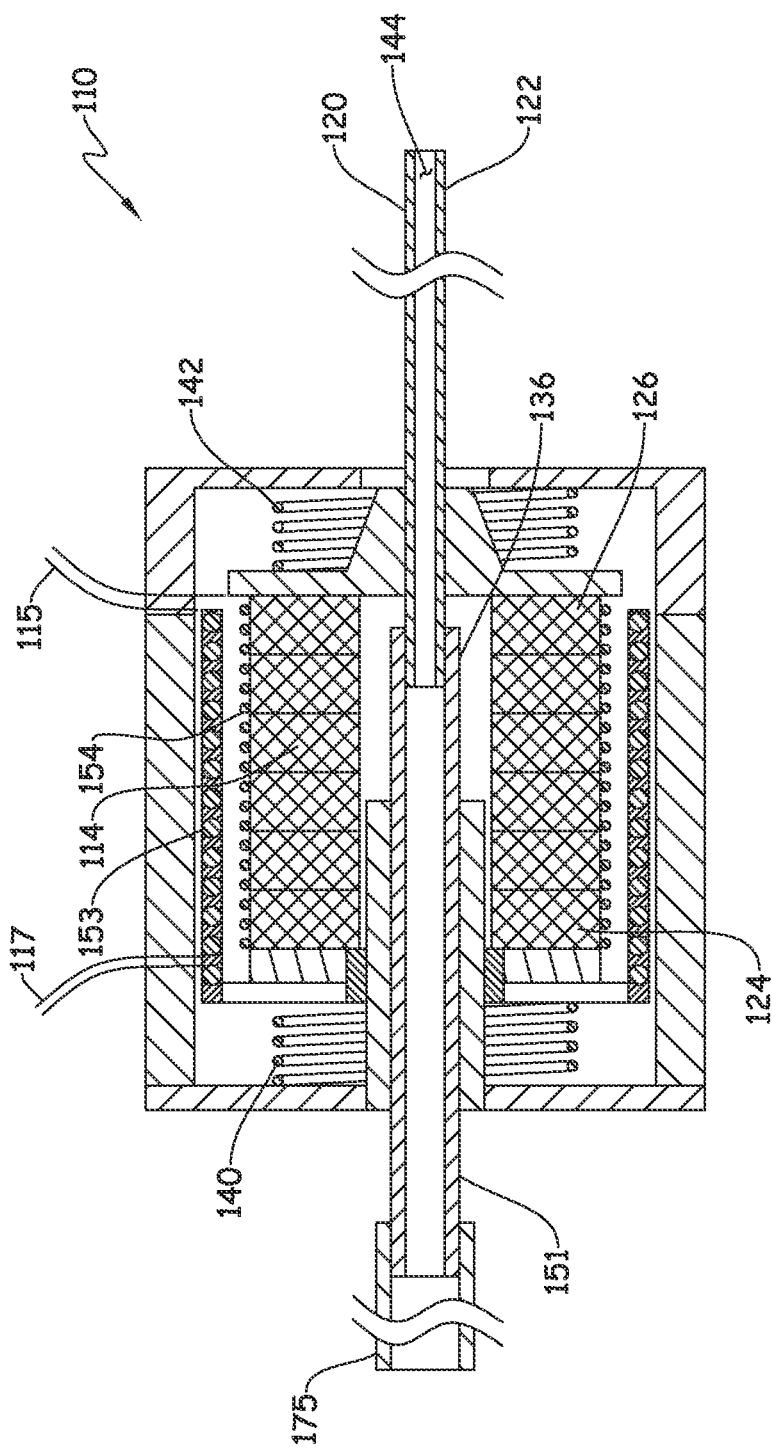
FIG. 3C is a side cross-sectional view of another alternative embodiment of the lithotripter of FIG. 3A, in accordance with the principles of the present disclosure.

Referring now to FIGS. 3A-3C, a variation of a lithotripter is illustrated and generally designated at 110. Like the lithotripter 10, the lithotripter 110 includes a driver housing 112 surrounding an ultrasonic driver 114 and a sonic driver 116. Thus, the ultrasonic driver 114 and the sonic driver 116 are disposed in a cavity 113 of the driver housing 112. The ultrasonic and sonic drivers 114, 116 may have the same operation and effect and be of the same type as described above with respect to the ultrasonic and sonic drivers 14, 16 of the lithotripter 10, and such discussion from above is herein incorporated by reference in this section. Lead wires 115 extend from the ultrasonic driver 114, and lead wires 117 extend from the sonic driver 116, so that the ultrasonic driver 114 and/or the sonic driver 116 may be excited by an electrical source (not shown). The sonic driver 116 is mechanically coupled to the ultrasonic driver 114, for example, by way of a connector 118. The connector 118 provides a rigid connection between the ultrasonic and sonic drivers 114, 116. Herein the sonic driver 116 is comprised of the coil 153 and the magnet 152. The magnet 152 is connected to the ultrasonic driver 114 by the connector 118.

In the present example, the ultrasonic driver 114 and the sonic driver 116 are disposed concentrically with one another within the driver housing 112. More specifically, the sonic driver 116 defines a cavity 167 therein, and the ultrasonic driver 114 is disposed in the cavity 167 of the sonic driver 116. The ultrasonic driver 114 has a proximal end 124 and a distal end 126, and the sonic driver 116 has a proximal end 128 and a distal end 130. The proximal end 124 of the ultrasonic driver 114 is disposed adjacent to the proximal end 128 of the sonic driver 116 within the cavity 167 of the sonic driver 116. The distal end 126 of the ultrasonic driver 114 is disposed adjacent to the distal end 130 of the sonic driver 116 within the cavity 167 of the sonic driver 116. Thus, the proximal ends 124, 128 of the ultrasonic and sonic drivers 114, 116 are disposed adjacent to a proximal end 132 of the driver housing 112, and the distal ends 126, 130 of the ultrasonic and sonic drivers 114, 116 are disposed adjacent to a distal end 134 of the driver housing 112. The sonic driver may be a magnet 152 working with a coil 153 or set of coils 153,154.

The ultrasonic and sonic drivers 114, 116 are coupled to the wave guide shaft 120 via a linear bearing 136, and the ultrasonic driver 114 is coupled to the wave guide shaft 120 with a connector 138. It is contemplated that the linear bearing 136 may be made of plastic or other lightweight materials. A first spring 140 is connected to one or both of the proximal ends 124, 128 of the ultrasonic and sonic drivers 114, 116, and the first spring 140 is connected to the proximal end 132 of the driver housing 112. A second spring 142 is connected to one or both of the distal ends 126, 130 of the ultrasonic and sonic drivers 114, 116, and the second spring 140 is connected to the distal end 134 of the driver housing 112. It is contemplated that either or both of the proximal and distal springs 140,142 may also be configured to act in place of a linear bearing, axially supporting and guiding the moving driver elements, thusly providing a linear bearing element function while also providing a necessary mechanical spring element function.

The lithotripter 110 has portions forming a lumen or channel therethrough for at least one of suctioning and irrigating a urinary tract. For example, the wave guide shaft 120 has a lumen 144 formed through the center of the wave guide shaft 120 and extending along the length of the wave guide shaft 120. In addition, the housing 112 has openings 146 formed through both the proximal and distal ends 132, 134 of the housing 112, and the ultrasonic and sonic drivers 114, 116 have a channel 147 formed through the center of the ultrasonic and sonic drivers 114, 116. Accordingly, the wave guide shaft 112 extends through the housing 112 and the ultrasonic and sonic drivers 114, 116. The wave guide shaft 120 may be rigid, semi-rigid, or flexible. Alternatively, rather than continuing uninterrupted through the entire handpiece assembly 112, the waveguide shaft 120 may terminate proximally at or within the distal end 38,138 of the ultrasonic driver 114 and, as an integral element of the ultrasonic driver 114, the central lumen 144 may continue therethrough and terminate immediately after exiting the proximal end 124 of the ultrasonic driver, as illustrated in FIGS. 3B and 3C. The central lumen 144 may continue on through the center of the sonic driver 116 as an attached tubular addendum to the central lumen at the proximal end 124 of the ultrasonic driver and terminate after exiting the proximal end of the housing 132 where it may connect to a suction tubing via suction connector 175 for the purposes of removing waste procedural fluids and stone fragments. Tubular addendum of the central lumen 151 originating within the wave guide shaft 120 and continuing through the ultrasonic driver 114 may be comprised of an alternate material, such as plastic. The connection between the tubular addendum of the central lumen 151 and the proximal end 124 of the ultrasonic driver 114 may be configured to limit interference with the ultrasonic vibration of the ultrasonic driver 114. Other configurations of the central lumen 144 and various connection methods of central lumen components may be utilized to minimize dampening effects on the ultrasonic vibration of the ultrasonic driver 114.

The rest of the description and operation of the lithotripter 10, which is not described as being different than the lithotripter 110 may be applied to the lithotripter 110, and such discussion is herein incorporated by reference into this section. For example, the closed loop feedback circuit of FIG. 2 may be applied to and used by the lithotripter 110 of FIG. 3.

Figure 4:
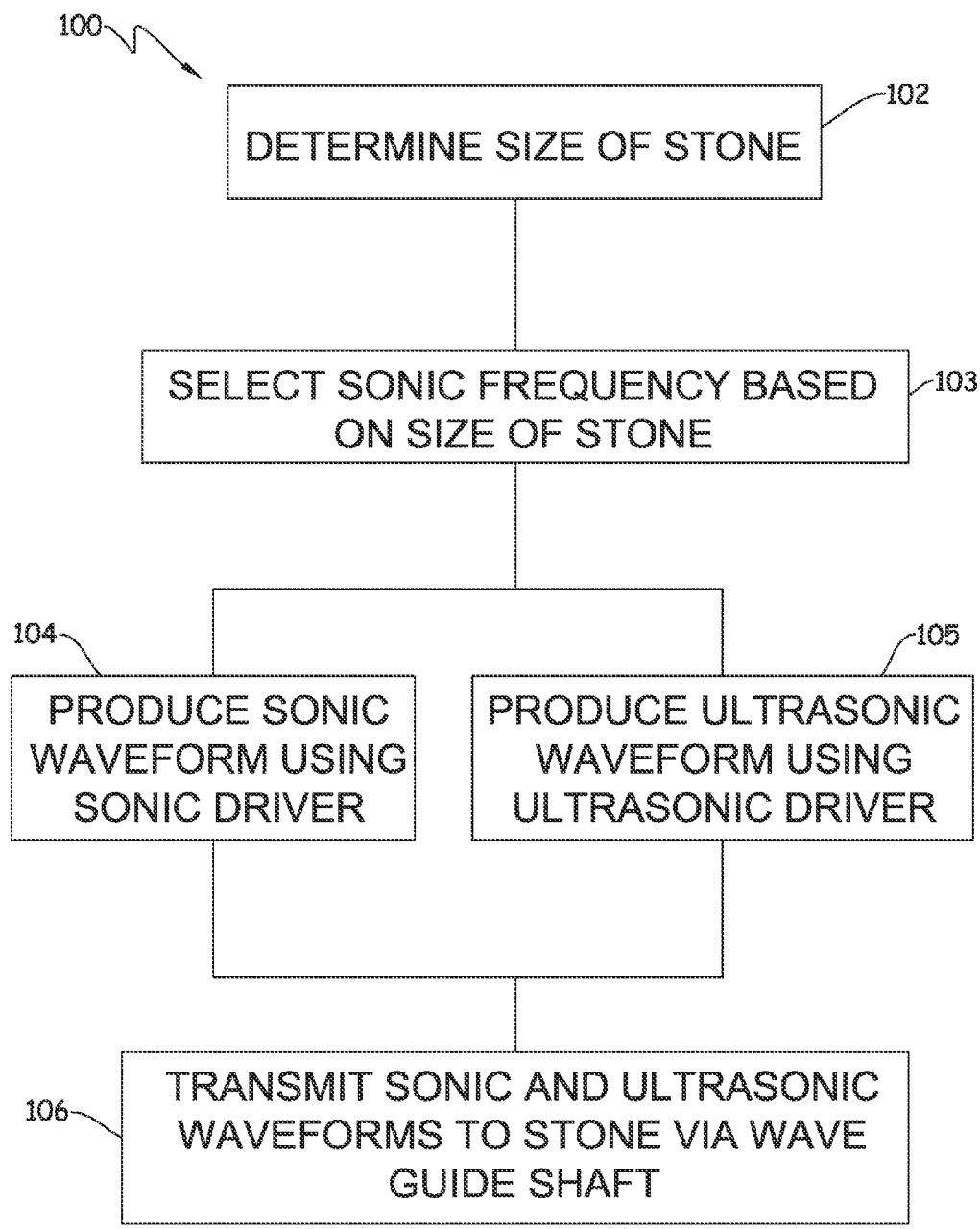
FIG. 4 is a block diagram illustrating a method for fragmenting stones, according to the principles of the present disclosure.

Referring now to FIG. 4, a method of fragmenting urinary tract stones using a lithotripter as claimed herein, such as the lithotripter 10, 110 described above, is illustrated and generally designated at 100. The method 100 includes a step 102 of determining a size, determining a type, or determining both a size and type of a urinary tract stone 66. The method 100 further includes a step 103 of selecting a magnitude of a sonic frequency for producing a sonic waveform, the magnitude of the sonic frequency being selected based on the size or type of the urinary tract stone 66. For example, the magnitude of the sonic frequency may be selected to correspond to the natural frequency of the target stone 66. The method 100 includes a step 104 of producing the sonic waveform using a sonic driver 16, 116. The method 100 includes a step 105 of producing an ultrasonic waveform having an ultrasonic frequency using an ultrasonic driver 14, 114. The steps 104, 105 may be completed simultaneously, if desired, or alternatively, serially. The method 100 includes a step 106 of transmitting the sonic waveform and the ultrasonic waveform to the urinary tract stone 66 via a wave guide shaft 20, 120.

When performing the method 100, the magnitude of the sonic frequency may be provided at about the natural frequency of the urinary tract stone 66. In addition, or in the alternative, the magnitude of the sonic frequency may be selectable from at least a low sonic frequency, a medium sonic frequency, and a high sonic frequency. For example, the low sonic frequency may be provided in the range of about 0.3-16 Hz, the medium sonic frequency may be provided in the range of about 16-70 Hz, and the high sonic frequency may be provided in the range of about 70-200 Hz. The ultrasonic frequency may be provided in the range of about 20-30 kHz. The ultrasonic waveform may be provided having an ultrasonic waveform amplitude in the range of about 10-50 micrometers, and the sonic waveform may be provided having a sonic waveform amplitude in the range of about 0.5-2 millimeters.

The method 100 may also include suctioning and/or irrigating a urinary tract through a lumen 44, 144 extending through the wave guide shaft 20, 120 and thus, through channels 48, 50, 147 formed in the ultrasonic and sonic drivers 14, 114, 16, 116.

In addition, the method 100 may include electronic gating the ultrasonic waveform with a square wave of variable frequency and duty cycle, as described above.

Figure 5:
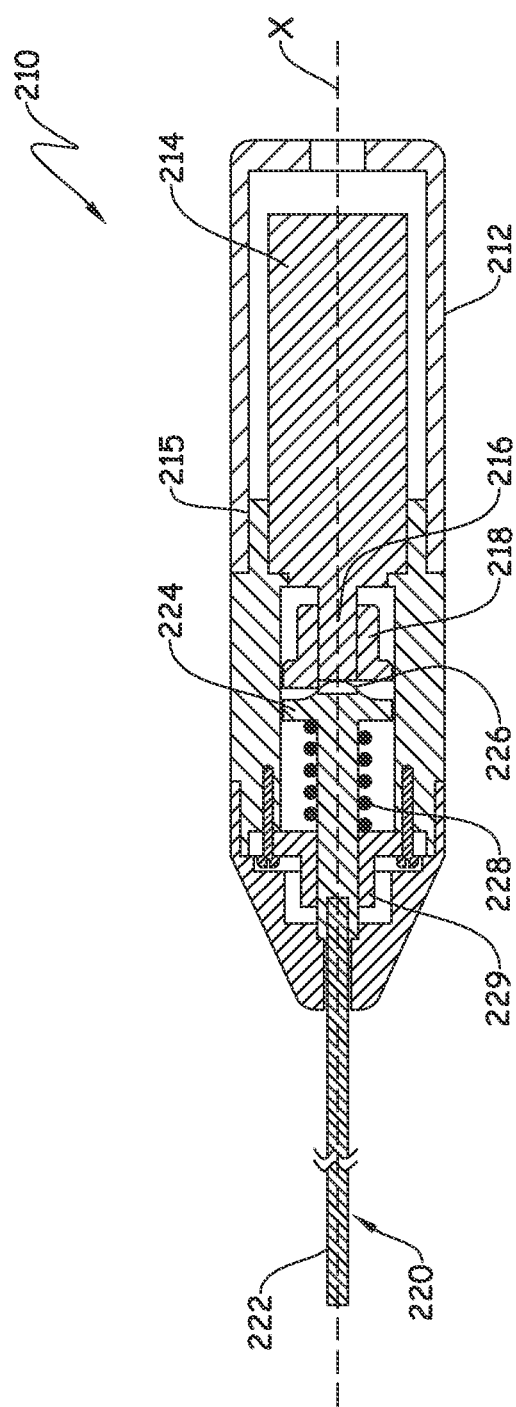
FIG. 5 is a side cross-sectional view of yet another lithotripter for fragmenting stones, in accordance with the principles of the present disclosure.
Figure 6C:
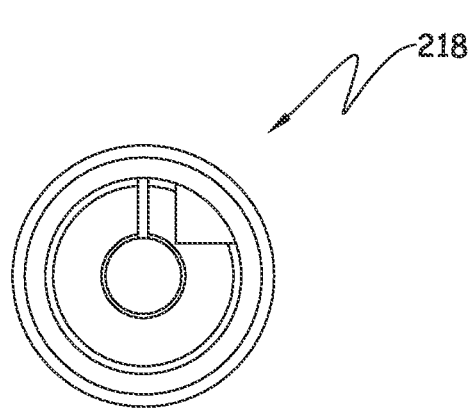
FIG. 6C is an end view of the motor coupler of the lithotripter of FIGS. 6A-6B, according to the principles of the present disclosure.
Figure 6A:
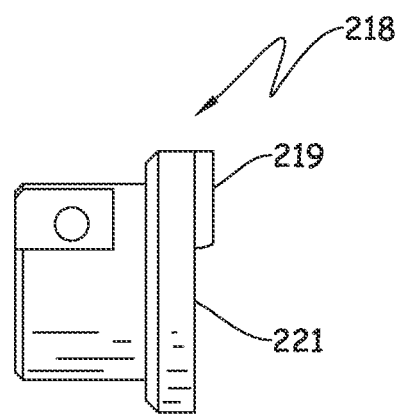
FIG. 6A is a right side view of a motor coupler of the lithotripter of FIG. 5, according to the principles of the present disclosure.
Figure 6D:
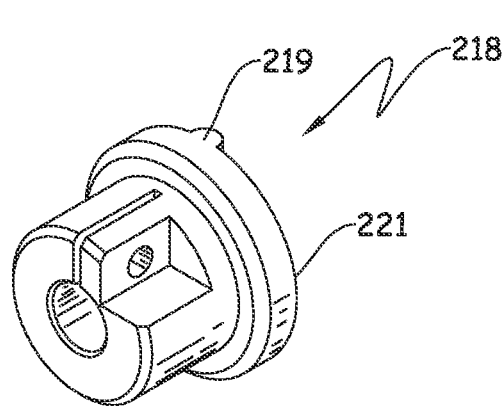
FIG. 6D is a perspective view of the lithotripter of FIGS. 6A-6C, in accordance with the principles of the present disclosure.
Figure 6B:
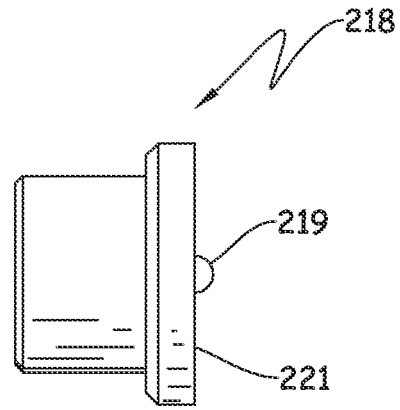
FIG. 6B is a left side view of the motor coupler of FIG. 6A, in accordance with the principles of the present disclosure.

Referring now to FIG. 5, a variation of a lithotripter is illustrated and generally designated at 210. The lithotripter 210 is configured to fragment a stone in a patient's body, such as in a patient's ureter, kidney, or bladder. The lithotripter 210 includes a housing 212 having a brushless DC motor 214 disposed in the housing 212. The brushless DC motor 214 is operable to produce a rotational motion. The brushless DC motor 214 may be autoclavable and may have three Hall Effect sensors, by way of example. The motor 214 may be mounted into a holder portion 215 of the housing, for example, with threading.

A motor shaft 216 extends from a rotor of the brushless DC motor 214 and is operable to be rotated along a longitudinal axis X of the lithotripter 210. A motor coupler 218 is attached to the motor shaft 216, which is also illustrated in FIGS. 6A-6D. For example, as shown in FIGS. 6A-6D, the motor coupler 218 is annular and has an extension 219 extending from an end face 221. The motor coupler 218 may be formed of hard steel.

A probe coupler 224 having a cam surface 226 is disposed in the housing 212 adjacent to the motor coupler 218. The probe coupler 224 is also illustrated in FIGS. 7A-7D. For example, the probe coupler has an elongate cylindrical shaft 225 extending from an end 227. The end 227 has the cam surface 226 formed thereon. The probe coupler 224 (including the cam surface 226) and the motor coupler 218 form a mechanical motion converter, wherein the rotational motion produced by the motor 214 is converted to a linear oscillating motion of the probe coupler 224, producing a linear waveform. It is contemplated that the cam surface 226 may be sloped to encourage production of a greater shock.

A spring 228 biases the probe coupler 224 into contact with the motor coupler 218, and when the motor coupler 218 is rotated, it slides along the cam surface 226 and causes the probe coupler 224 to move back and forth along the longitudinal axis X. It is contemplated that the spring 228 may further comprise a dampening feature. The extensions 219 of the motor coupler 218 contact the cam surface 226 of the probe coupler 224 as the motor coupler 218 rotates about a center of the motor coupler 218. The motor coupler 218 therefore pushes the probe coupler 224 along the longitudinal axis X of the lithotripter 210 in one direction along the longitudinal axis, and the spring 228 biases the probe coupler 224 in the opposite direction along the longitudinal direction X, thereby moving the probe coupler 224 in the opposite direction when the extension 219 of the motor coupler 218 is rotated away from a high portion 231 of the cam surface 226. It is contemplated that the cam surface may be sloped to create a greater shock. It is contemplated that the cam surface may be hardened and ground to reduce wear potential. A linear bearing 229 may be disposed adjacent to the spring 228, which reduces the friction of linear movement. It is contemplated that linear bearing the 229 may be made of plastic or other lightweight materials.

A wave guide shaft 220 is coupled to the probe coupler 224. The wave guide shaft 220 is configured to transmit the linear waveform to a target stone. For example, when the distal end 222 of the wave guide shaft 220 is placed into contact with a target stone, it may produce a jackhammer effect thereon. Thus, the housing 212 may be a handle and the wave guide shaft 220 extends therefrom.

Figure 10:
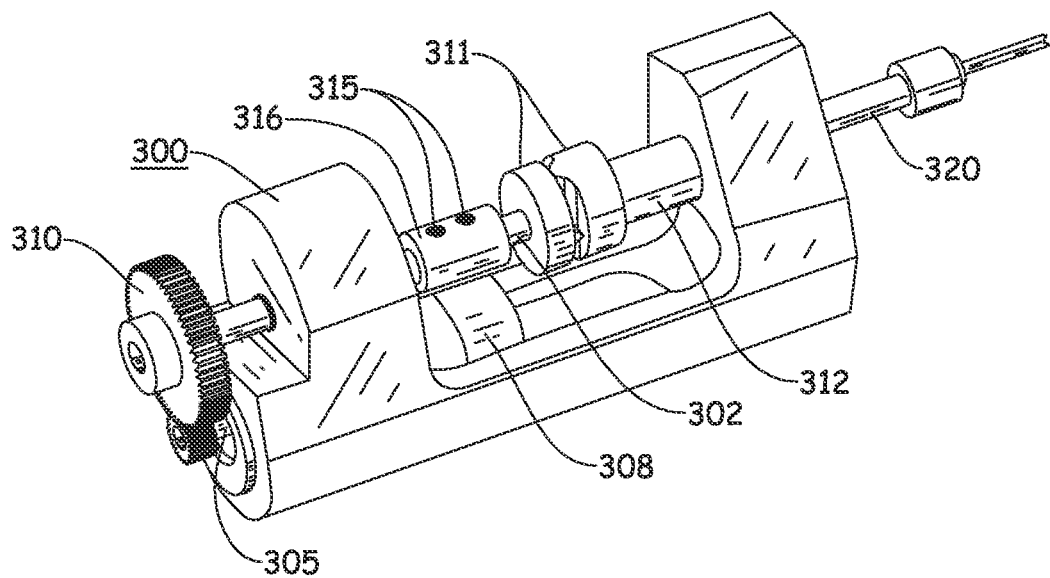
FIG. 10 is a perspective view of one embodiment of the brushless DC motor assembly of a lithotripter, in accordance with the principles of the present disclosure.
Figure 11:
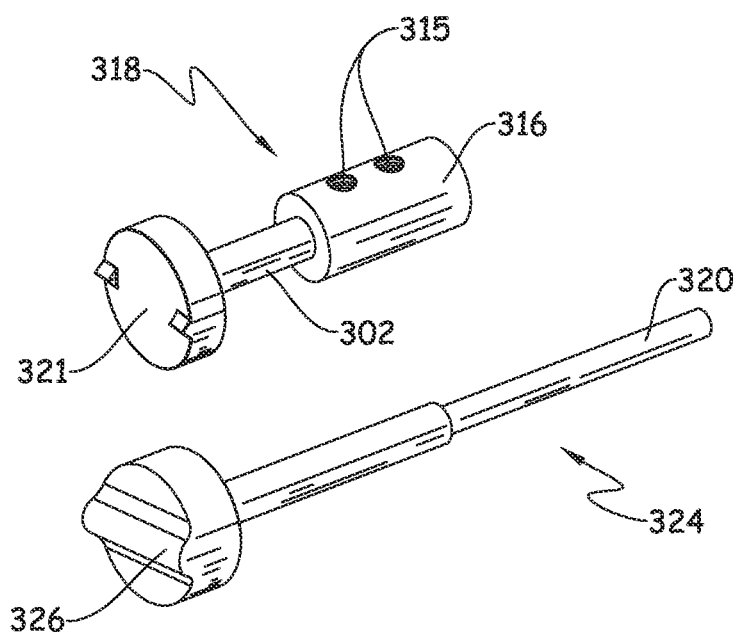
FIG. 11 is a perspective view of a motor coupler and probe coupler, in accordance with the principles of the present disclosure.

It is contemplated that in some embodiments the motor shaft 305 may be separate from a cam shaft 302 as depicted in FIGS. 10-11. Isolating the motor shaft 305 from the cam shaft 302 may serve to protect the integrity of the motor over time, as illustrated in FIG. 10. It is contemplated that a gear assembly 310 would transfer energy from the BLDC motor shaft 305 to the cam shaft 302. This gear assembly 310 may be in a 1:4 ratio, allowing for amplification of the energy output from the motor. The cam shaft 302 may include a dampening mechanism 312 at a proximal end, which may include a section of silicone and may be further supported with an internal spring within the section of silicone placed between the cam pair 311 and the lithotripsy shaft 320, formed together to surround the cam shaft 302 and provide dampening of the vibrational and/or linear motion during operation. It is contemplated that bearings and silicone may be provided at points where the cam shaft 302 and motor shaft 305 connect into the housing 300. In some embodiments, a motor coupler 318 is provided with a motor coupler attachment block 316 which allows for the option of swapping out a cam pair 311, which represents the transfer point between motor coupler and shaft coupler, to correct for wear during regular maintenance, for example. The motor coupler 318 and the motor coupler attachment block 316 may be easily loosened and removed using set screws 315 in order to insert a replacement motor coupler 318. It is contemplated that a suction or irrigation capability may be provided through the cam shaft 302 as this shaft is located toward a centerline of the device.

FIG. 11 illustrates a close up view of the motor coupler 318 and the probe coupler 324. The motor coupler 318 (including end surface 321) is disposed in the housing 300 adjacent to the shaft coupler 324 (including the cam surface 326). The motor coupler 318 is removable and replaceable, in some embodiments, by loosening the set screws 315 in the motor coupler attachment block 316. The motor coupler connects to the cam shaft 302 and the probe coupler connects to the wave guide shaft 320.

Figure 8:
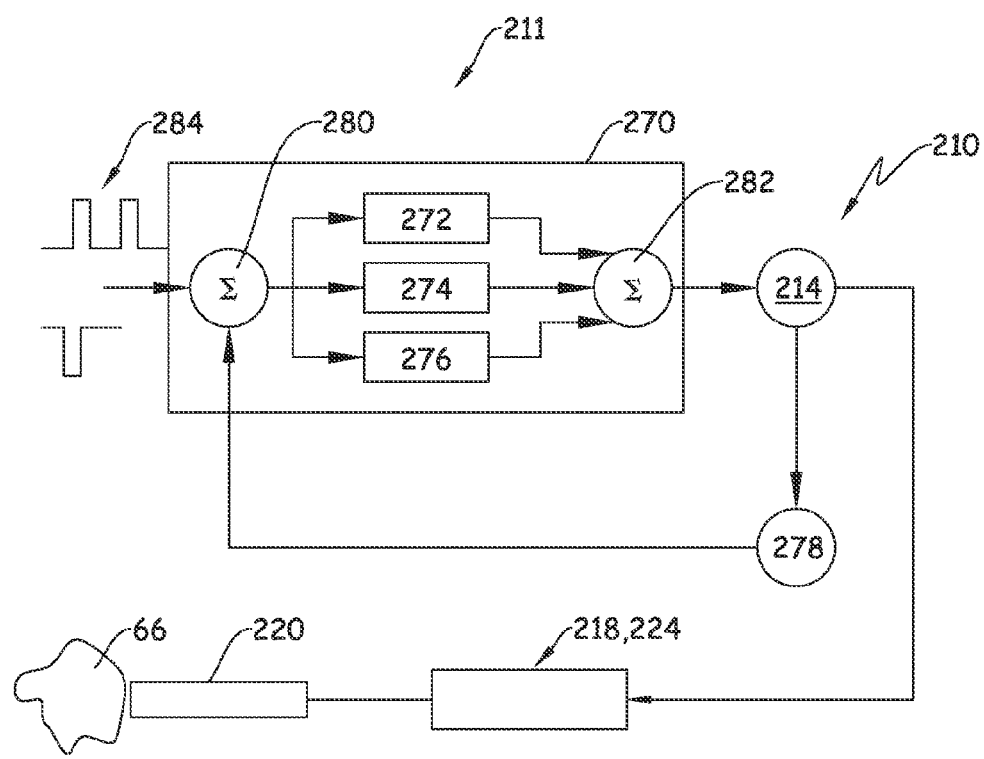
FIG. 8 is a block diagram illustrating a lithotripter assembly for use with the lithotripter of FIG. 5, in accordance with the principles of the present disclosure.

The lithotripter 210 may be provided as part of a lithotripter assembly 211 that also includes a controller 270, or driver/amplifier (see FIG. 8). The controller 270 may be configured to operate the brushless DC motor 214 in at least a first mode of operation and a second mode of operation. The first mode of operation may be an over-shoot impulse mode and the second mode of operation may be a high speed rotational mode.

For example, the brushless DC motor 214 has a rotor coupled to the rotational shaft 216. In the over-shoot impulse mode, an impulse torque is generated by the brushless DC motor by moving the rotor in a partial rotation; the rotor and the rotational shaft 216 may be moved in at least one step of less than a full rotation of the rotor to generate a torque on the wave guide shaft 220. In one example, the rotor and rotational shaft 216 may be moved in a plurality of back-and-forth steps of between about ten and thirty degrees, or about 15 degrees in the over-shoot impulse mode, which provides a high torque on the wave guide shaft 220. In the over-shoot impulse mode, the controller 270 works on a current mode and a large amplify gain is applied to the current loop. For example, a current of about 20 Amps could be applied to the controller 270 for a short period. Accordingly, a high torque can be applied to the stone 66 with the over-shoot impulse mode, which can have a ballistic effect on the stone 66. The amplify gain can be programmed to adapt to different size stones, using the feedback loop illustrated in FIG. 8.

In the high speed rotational mode, the brushless DC motor 214 operates the rotor and rotational shaft 216 in a continuous rotational motion. A constant control voltage may be applied to the amplifier of the controller 270, and the motor 214 may rotate at a speed of up to about 50,000 rpm or even 60,000 rpm. Therefore, in the high speed rotational mode, the rotor and rotational shaft 216 may rotate of speeds of about 40,000 to about 60,000 rpm. In one variation, a voltage of about 0-10 V may be applied to the controller 270, for example, about 5V, in the high speed rotational mode.

Figure 9:
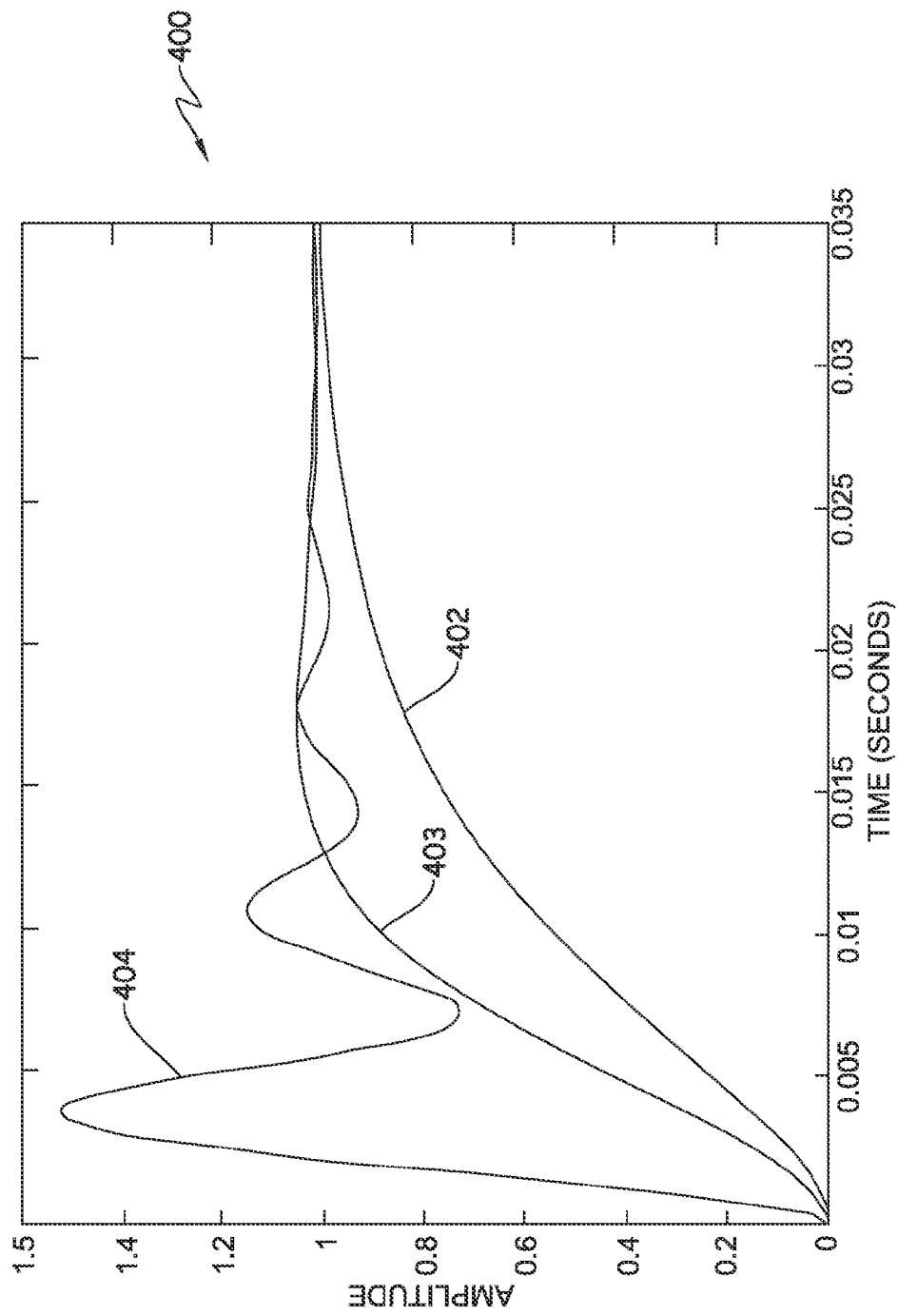
FIG. 9 is a graph illustrating a closed loop step of a lithotripter assembly for use with the lithotripter of FIG. 5, showing amplitude of oscillation as a function of time, in accordance with the principles of the present disclosure.

Referring to FIG. 9, a graph 400 illustrates the amplitude of the oscillation of the wave guide shaft 220 as a function of time. When the lithotripter 210 is in the over-shoot impulse mode, a high amplitude of oscillation is provided for a short period of time, as illustrated by the impulse mode plot line 404. When the lithotripter 210 is in the high speed rotational mode, a moderate and continuous amplitude is provided as illustrated by the rotational plot line 403. Plot line 402 shows the motion of the motor 14 when a small proportional gain is applied in the controller 270.

Referring again to FIG. 8, the controller 270 may be a proportional-integral-derivative (PID) controller, having a proportional 272, integral 274, and derivative 276 control logic. The lithotripter assembly 211 may also include a position feedback sensor 278, such as an optical encoder, to determine the position of the rotor of the motor 214. The position feedback sensor 278 is configured to provide rotor position data to the PID controller 270. The position sensor may provide the rotor position date to a summation point 280 within the PID controller, which then updates the control logic and provides the control logic to a summation point 282 and ultimately to the motor 214. A power source 284 provides a power input to the controller 270, which may be capable of providing a high power for the over-shoot impulse mode and a lower power for the high speed rotational mode, or vice versa.

Thus, in the over-shoot impulse mode, the motor 214 is driven by a high performance servo driver 270 in current mode. The position sensor 278 is located in the update loop. The loop may be set to repeat at 0.5 ms intervals, for example. The torque provided may be explained by the following equation: $\tau = K_p(\theta_2 - \theta_1) + K_d(\omega_2 - \omega_1)$, where $\tau$ is the torque provided to the stone 66 via the wave guide shaft 220, $K_p$ is the proportional gain, $\theta_2$ is the rotor final angular position in one loop, $\theta_1$ is the initial rotor angular position in one loop, $K_d$ is the derivative gain, $\omega_2$ is the final angular velocity of the rotor in one loop, and $\omega_1$ is the initial angular velocity of the rotor in one loop. $\omega_2 = d\theta_2/dt$ and $\omega_1 = d\theta_1/dt$.

In some embodiments where the cam shaft 302 is positioned along a separate longitudinal axis from a central axis of the motor shaft 305 and a gear assembly 310 is provided to transfer energy between the cam shaft 302 and the motor shaft 305, torque values may range from about 112 mNm to about 144 mNm for a spur gear with gear ratio 1:4. Resulting rotational speeds for this embodiment would range from about 2500 rpm to about 7500 rpm.

As in the examples above, the oscillation of the wave guide shaft 220, 320 may be provided to the stone 66 at a frequency that is about equal to the natural frequency of the stone 66.

The natural frequency of the stone may vary based on stone size. It is contemplated that various modes of operation may be employed with the lithotripter described herein. By way of example, three ranges may be provided as described above or may be more generalized as small stone mode, large stone mode, and general mode. Small stone mode may provide oscillation frequencies in the range of 17-170 Hz, for example. Large stone mode may provide oscillation frequencies in the range of 0.5-17 Hz, for example. General mode may provide oscillation frequencies in the range of 0.5-170 Hz, for example.

In an automatic mode of operation, the device may start with operation in general mode and then upon detection of a large stone or small stone through use of a sensor, for example, proceed to operate in that mode. If at first a large stone mode is utilized, the device may switch to operation in a small stone mode after a predetermined period of time, such as 30 seconds to 1 minute, for example.

In another embodiment, a manual mode of operation may be utilized. In this mode, a user may select whether or not to operate in large stone mode, small stone mode, or general mode based on direct observation through the distal tip of an endoscope, for example.

It is further contemplated that the device may be provided with a sharp tip which may facilitate stones maintaining contact with the tip during lithotripsy after use of a suction function to attract a stone to the distal end of the device and may further limit size of outgoing fragments during active lithotripsy and may help to enhance the stone free rate by producing smaller particle sizes which can be removed by suction through the lithotripsy shaft 20. It is contemplated that a tip element passage may be provided with various alternative configurations, including a four point crimped tip with countersunk sections, a four slot angled tip with sloped tab ends, a four slot angled tip with sloped tab ends and one side of the tabs bent in, a tip with two slots cut into opposing sides, a divided tip with an optional insert, and a tip with four slots cut in and two inserts with sloped tab end faces. Examples of such tip elements are provided in FIGS. 12-28.

Figure 12:
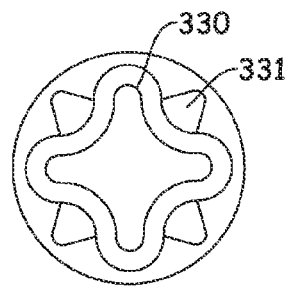
FIG. 12 is an end view of one embodiment of a distal tip section of a lithotripter, in accordance with the principles of the present disclosure.
Figure 13:
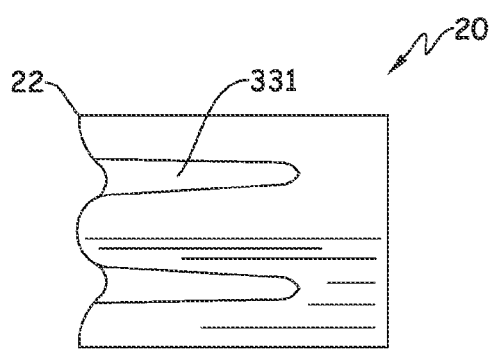
FIG. 13 is a side view of the distal tip section of FIG. 12, in accordance with the present disclosure.

FIGS. 12-13 illustrate an end and a side view of a distal end of an example embodiment of a tip element which may be provided on wave guide shaft 20 at a distal end 22. A crimped tip 330 is combined with countersunk sections which extend from the distal end 22 toward the proximal end of the wave guide shaft 20.

Figure 14:
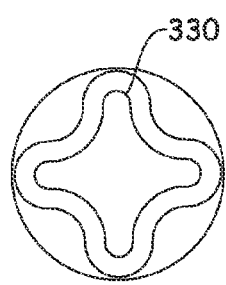
FIG. 14 is an end view of one embodiment of a distal tip section of a lithotripter, in accordance with the principles of the present disclosure.
Figure 15:
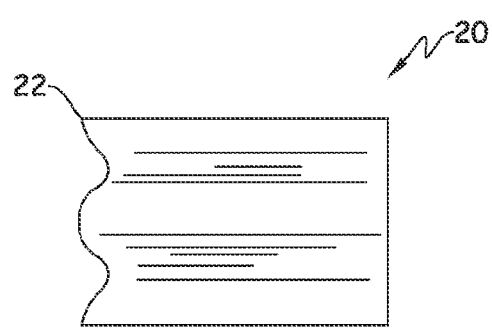
FIG. 15 is a side view of the distal tip section of FIG. 14, in accordance with the present disclosure.

FIGS. 14-15 illustrate an alternative embodiment which includes a crimped tip 330 provided at the distal end 22 of the wave guide shaft 20.

Figure 16:
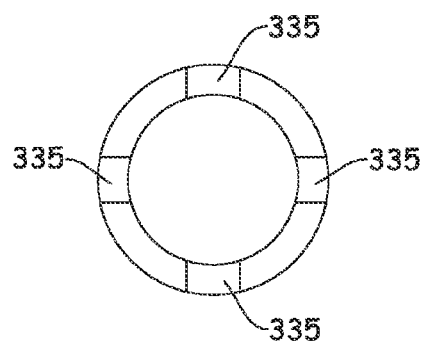
FIG. 16 is an end view of one embodiment of a distal tip section of a lithotripter, in accordance with the principles of the present disclosure.
Figure 17:
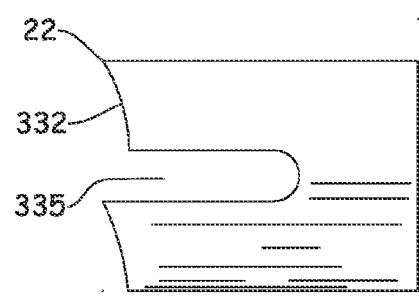
FIG. 17 is a side view of the distal tip section of FIG. 16, in accordance with the present disclosure.
Figure 18:
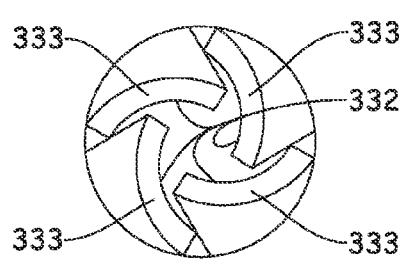
FIG. 18 is an end view of one embodiment of a distal tip section of a lithotripter, in accordance with the principles of the present disclosure.
Figure 19:
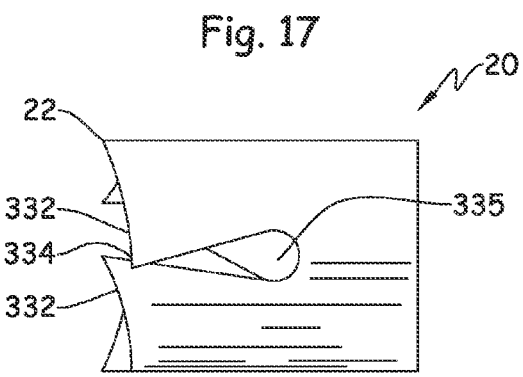
FIG. 19 is a side view of the distal tip section of FIG. 18, in accordance with the principles of the present disclosure.

FIGS. 16-17 illustrate an alternative embodiment which includes four slots 335 provided at a distal end and also includes angled tip regions 332 at the distal end 22 of the wave guide shaft 20. FIGS. 18-19 illustrate an alternative embodiment which includes sloped tab ends 333 as well as bent in portions 334, which add an element of contouring to the distal most region which may provide an additional distribution of sharp surfaces for kidney stones to maintain contact with the distal end 22, of the shaft 20. This embodiment illustrates the tabs bent in at one edge in order to reduce the cross-sectional opening area of the tube to reduce the size of the stone fragments entering the tube, increase the affected area of the stone being fragmented, provide a wedging effect to more effectively split up a stone and reduce the overall size of the stone fragments produced. The inclusion of side slots also improves irrigation and enhances the evacuation of smaller stone debris which might otherwise intervene between the shaft tip and the stone being fragmented and thus reduce the lithotripter's stone fragmenting effectiveness by dampening the direct impact of the lithotripter shaft tip on the stone being fragmented.

Figures 20, 21:
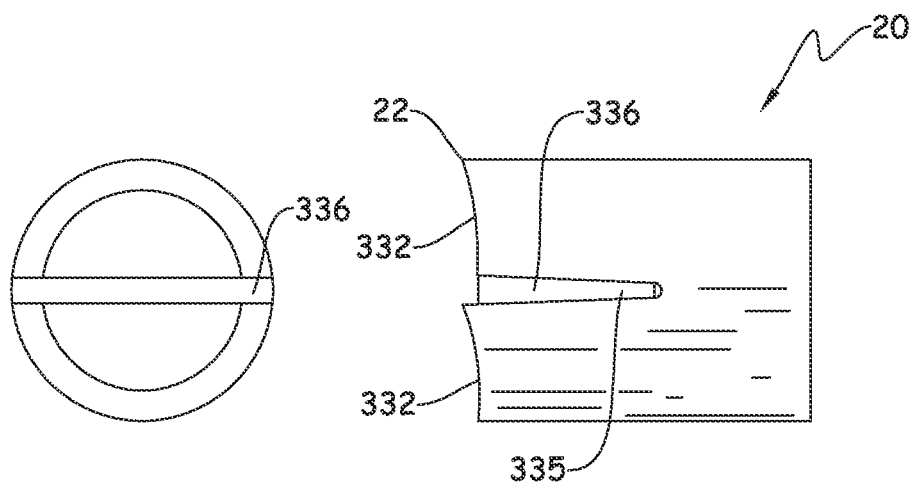
FIG. 20 is an end view of one embodiment of a distal tip section of a lithotripter, in accordance with the principles of the present disclosure.
FIG. 21 is a side view of the distal tip section of FIG. 20, in accordance with the present disclosure.

FIGS. 20-21 illustrate an additional alternative embodiment in which an insert 336 is placed into slots 335 and an angle 332 is applied to the distal most region 22 of the wave guide shaft 20. This embodiment illustrates the addition of a cross-member in order to reduce the cross-sectional opening area of the tube to reduce the size of the stone fragments entering the tube, increase the affected area of the stone being fragmented and more effectively split up a stone and reduce the overall size of the stone fragments produced. Inclusion of side slots could also improve irrigation and enhance the evacuation of smaller stone debris which might otherwise intervene between the shaft tip and the stone being fragmented and thus reduce the lithotripter's stone fragmenting effectiveness by dampening the direct impact of the lithotripter shaft tip on the stone being fragmented. In this example the insert is wider at the face of the tube than it is down inside the tube, to reduce the possibility of clogging at the tip by providing an ever widening cross-section from the distal face of the shaft tip to the proximal direction of the shaft. Inserts such as this may be brazed or welded to the lithotripsy shaft to secure them in place.

Figure 22:
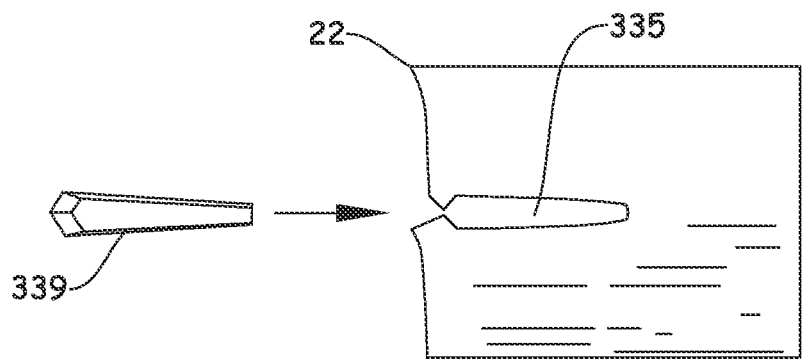
FIG. 22 is a side view of one embodiment of a distal tip section of a lithotripter, in accordance with the principles of the present disclosure.
Figure 23:
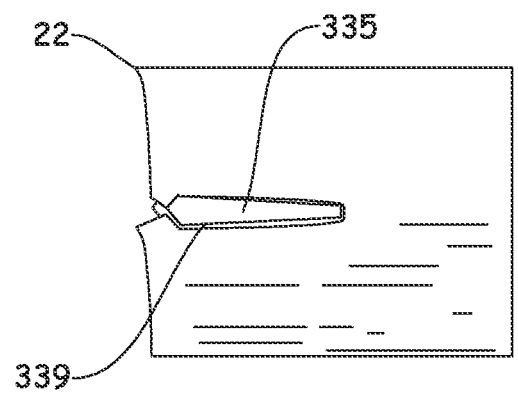
FIG. 23 is a side view of the distal tip section of FIG. 22, in accordance with the principles of the present disclosure.

FIGS. 22-23 illustrate an embodiment where one or more insert slots may be provided with interlocking or retaining features for maintaining a position of the insert in slots 335 within the distal tip 22 of the lithotripter shaft tip. Interlocking features may include grooves, beveled edges, or tabs and slots. These mechanical retaining features are meant to assist in placement of the inserts as well as augment retention of the inserts in addition to welding or brazing or the like of the inserts to the lithotripsy shaft.

Figures 24, 25:
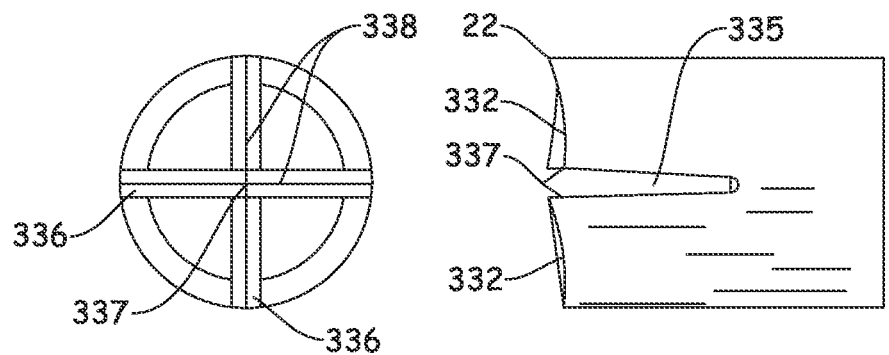
FIG. 24 is an end view of one embodiment of a distal tip section of a lithotripter, in accordance with the principles of the present disclosure.
FIG. 25 is a side view of the distal tip section of FIG. 24, in accordance with the present disclosure.

FIGS. 24-25 illustrate an alternative embodiment in which two inserts 336 are placed perpendicularly with respect to each other into slots 335 to improve fragmentation effectiveness and further limit kidney stone particle size which may enter the wave guide shaft 20 during active suction. Edges of the inserts 336 may additionally be provided with sharp surfaces 338 for enhancing the ability of stones to maintain contact with the distal end 22 as well as fragment stones more effectively. In this embodiment, shaft tabs are additionally provided with an angled tip 332 to more effectively engage with the surface of a stone. The inserts may be wedged shaped with a narrower proximal edge to reduce the possibility of clogging.

Figure 26:
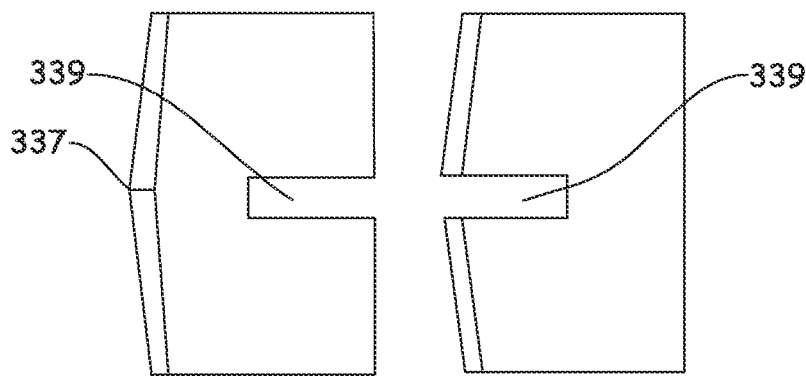
FIG. 26 is a side view of one embodiment of inserts to be placed into a distal tip section of a lithotripter, in accordance with the principles of the present disclosure.
Figure 27:
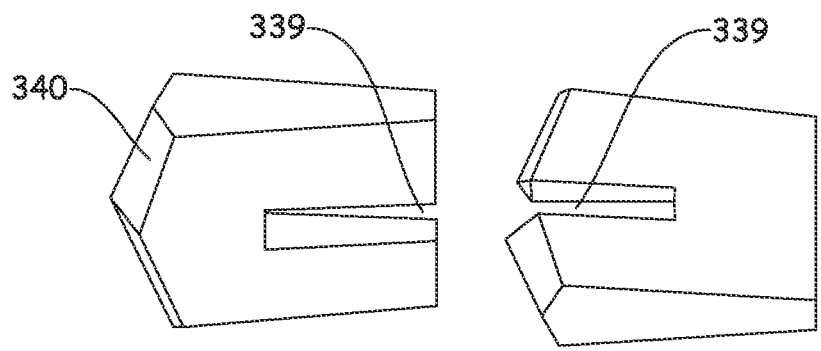
FIG. 27 is a side view of one embodiment of inserts to be placed into a distal tip section of a lithotripter, in accordance with the present disclosure.

FIGS. 26-27 represent an embodiment of inserts with interlocking features of the distal end 22 of the waveguide shaft 20. A left insert may be rotated and placed on top of a right insert such that they form a tight immovable fit through the use of interlocking features, in the present example via slots cut into the inserts.

Figure 28:
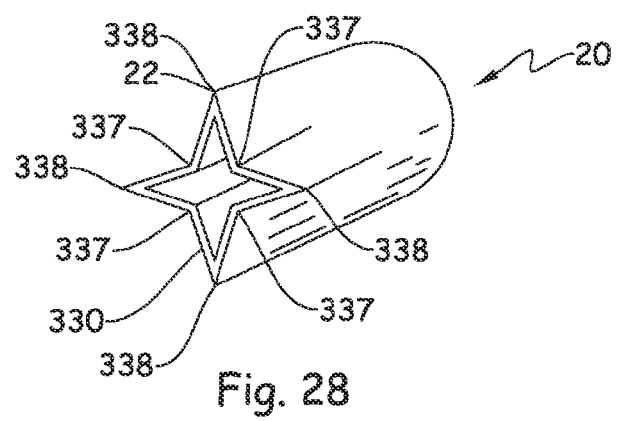
FIG. 28 is a perspective view of the distal tip section of a lithotripter, in accordance with the principles of the present disclosure.
Figures 29, 30:
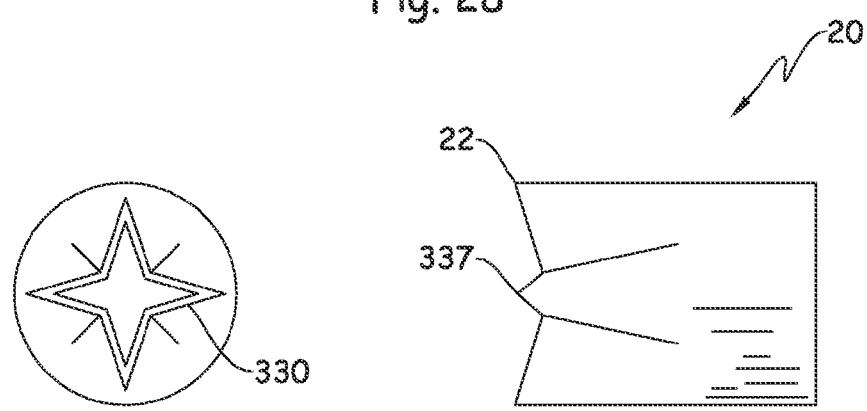
FIG. 29 is an end view of a distal tip section of a lithotripter, in accordance with the principles of the present disclosure.
FIG. 30 is a side view of a distal tip section of a lithotripter, in accordance with the principles of the present disclosure.

FIGS. 28-30 represent an alternative embodiment of the distal end 22 of the wave guide shaft 20 with a crimped tip 330. The crimped tip 330 is provided with sharp corners 337 and pointed edges 338 to enhance the ability of kidney stones to maintain contact to waveguide shaft 20 during stone breaking or active suction. A smaller distal opening reduces the size of the evacuated fragments.

Figures 31, 32:
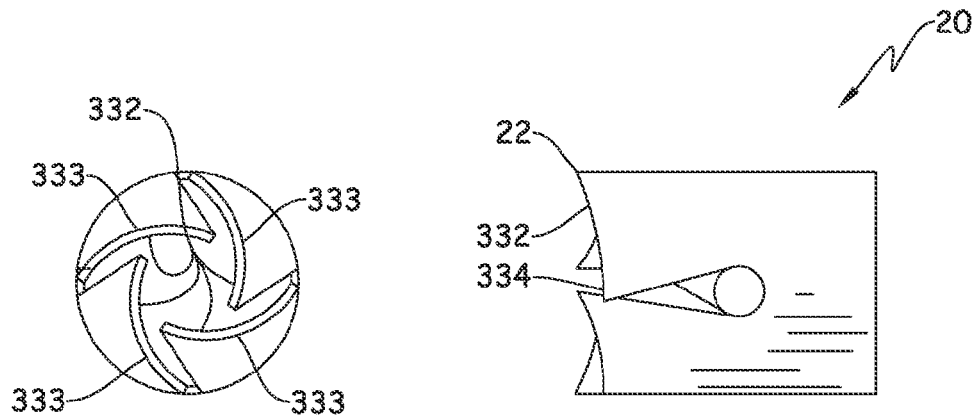
FIG. 31 is an end view of a distal tip section of a lithotripter, in accordance with the principles of the present disclosure.
FIG. 32 is a side view of a distal tip section of a lithotripter, in accordance with the principles of the present disclosure.

Similarly to FIGS. 18-19 but with a thinner side wall, FIGS. 31-32 illustrate an alternative embodiment of sharp features which may be provided to the distal end 22 to wave guide shaft 20. Four slots 335 are cut extending from the distal end 22 towards the proximal end and sloping 333 and angling 332 is provided at the tip ends.

Figure 33:
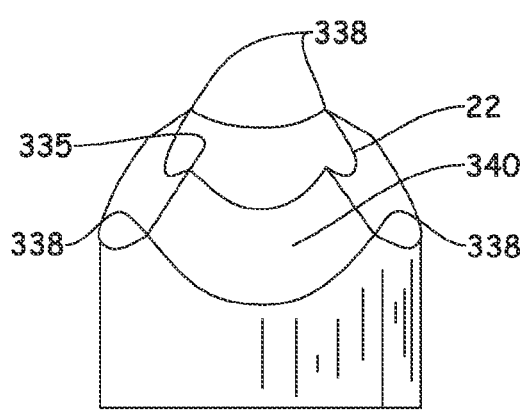
FIG. 33 is a perspective view of a distal tip section of a lithotripter, in accordance with the principles of the present disclosure.
Figure 34:
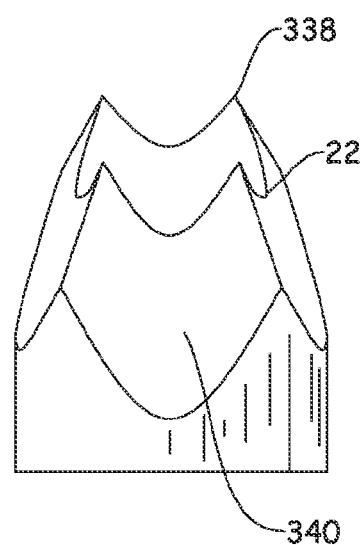
FIG. 34 is a perspective view of a distal tip section of a lithotripter, in accordance with the principles of the present disclosure.
Figure 35:
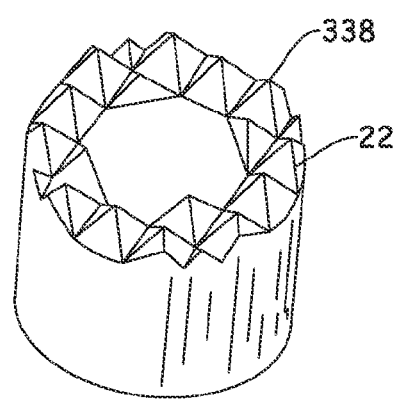
FIG. 35 is a perspective view of a distal tip section of a lithotripter, in accordance with the principles of the present disclosure.
Figure 36:
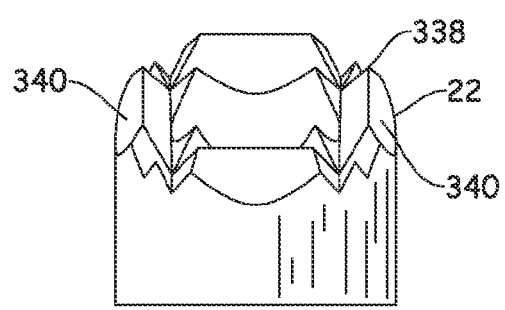
FIG. 36 is a perspective view of a distal tip section of a lithotripter, in accordance with the principles of the present disclosure.

FIGS. 33-36 show lithotripsy shaft tips which have been modified from a flat terminal face by various beveling or angled cutting methods. FIGS. 33-34 illustrate simple external, planar beveling of a lithotripsy shaft tip. This type of tip provides sharp points and edges for "digging into" stone surfaces as well as wedging action for splitting stones apart. FIGS. 35-36 present examples of lithotripsy shaft tip faces which have had multiple, angled cuts made, producing sharp, pyramidal and/or ridged points or edges which would enhance the ability of such tips to "dig in" to a stone surface. In both these examples, a tube tip could be augmented with bending or additional material via brazing, welding or the like prior to the surface modification so that an opening smaller than the original tube's internal diameter may be presented, to limit the size of the stone fragments entering the tube during suction. The type of tip configurations represented in FIGS. 35-36 are expected to have a lower possibility of inadvertent tissue damage due to direct contact as the pointed elements are more numerous, closely positioned and effectively less aggressive than those examples represented in FIGS. 33-34, for example.

The description of the invention is merely exemplary in nature and variations that do not depart from the gist of the invention are intended to be within the scope of the invention. Such variations are not to be regarded as a departure from the spirit and scope of the invention. For example, variations in the various figures can be combined with each without departing from the spirit and scope of the present disclosure.

The preferred embodiment of the present invention has been disclosed. A person of ordinary skill in the art would realize, however, that certain modifications would come within the teachings of this invention. Therefore, the following claims should be studied to determine the true scope and content of the invention.

Any numerical values recited in the above application include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints, the use of "about" or "approximately" in connection with a range apply to both ends of the range. Thus, "about 20 to 30" is intended to cover "about 20 to about 30", inclusive of at least the specified endpoints.

The disclosures of all articles and references, including patent applications and publications, are incorporated by reference for all purposes.

The term "consisting essentially of" to describe a combination shall include the elements, ingredients, components or steps identified, and such other elements ingredients, components or steps that do not materially affect the basic and novel characteristics of the combination.

The use of the terms "comprising" or "including" describing combinations of elements, ingredients, components or steps herein also contemplates embodiments that consist essentially of the elements, ingredients, components or steps.

What is claimed is:

1. A lithotripter for fragmenting urinary tract stones, the lithotripter comprising:
    an ultrasonic driver configured to produce an ultrasonic waveform having an ultrasonic frequency;
    a sonic driver configured to produce a sonic waveform having a sonic frequency selected according to a size of a urinary tract stone, the sonic driver being mechanically coupled to the ultrasonic driver;
    a stone size detector for detecting the size of the urinary tract stone, the stone size detector comprising at least one detector selected from a group of detectors consisting of an optical detector and an ultrasonic echo detector, the lithotripter being configured to automatically set at least one of the sonic driver or the ultrasonic driver to produce the sonic or ultrasonic waveform at the selected frequency according to the size of the urinary tract stone;
    a driver housing, the ultrasonic driver and the sonic driver being disposed within the driver housing; and
    a wave guide shaft for transmitting the ultrasonic and sonic waveforms to at least one urinary tract stone, the wave guide shaft being driven by at least one of the ultrasonic driver and the sonic driver.

2. The lithotripter of claim 1, wherein the sonic driver is an electromagnetic linear driver.

3. The lithotripter of claim 2, wherein the sonic driver is one of a voice coil motor, moving coil, moving magnet, and a dual coil, the ultrasonic driver being a piezoelectric stack.

4. The lithotripter of claim 2, wherein the lithotripter has portions forming a lumen therethrough for at least one of suctioning and irrigating a urinary tract.

5. The lithotripter of claim 2, wherein the ultrasonic driver and the sonic driver are disposed concentrically.

6. The lithotripter of claim 5, wherein the sonic driver has portions forming a cavity therein, the ultrasonic driver being disposed in the cavity of the sonic driver.

7. The lithotripter of claim 1, wherein the sonic frequency is about equal to a natural frequency of the at least one urinary tract stone.

8. The lithotripter of claim 1, wherein the ultrasonic driver and the sonic driver are disposed in series within the driver housing.

9. The lithotripter of claim 8, wherein the ultrasonic driver has a proximal end and a distal end, the sonic driver has a proximal end and a distal end, wherein the proximal end of the ultrasonic driver is disposed adjacent to the distal end of the sonic driver.

10. The lithotripter of claim 9, further comprising first and second springs.

11. The lithotripter of claim 1, wherein the lithotripter is configured to set the sonic driver to produce the sonic waveform at a first frequency if the urinary tract stone is greater than about 10 millimeters in diameter, a second frequency if the urinary tract stone is greater than about 2 millimeters and less than or equal to about 10 millimeters in diameter, and a third frequency if the urinary tract stone is less than or equal to about 2 millimeters in diameter.

12. The lithotripter of claim 11, wherein the first frequency is in the range of about 0.3-16 Hz, the second frequency is in the range of about 16-70 Hz, and the third frequency is in the range of about 70-200 Hz, and wherein the ultrasonic driver is configured to provide the ultrasonic waveform at an ultrasonic frequency in the range of about 20-30 kHz.

13. The lithotripter of claim 12, further comprising a closed loop feedback circuit configured to determine a preferred ultrasonic frequency that oscillates at a maximum amplitude.

14. The lithotripter of claim 12, wherein the wave guide shaft is rigid.

15. The lithotripter of claim 12, wherein the wave guide shaft is one of semi-rigid and flexible.

16. The lithotripter of claim 12, wherein the ultrasonic driver is configured to produce the ultrasonic waveform having an ultrasonic waveform amplitude in the range of about 10-50 micrometers, and wherein the sonic driver is configured to produce the sonic waveform having a sonic waveform amplitude in the range of about 0.5-2 millimeters.

17. The lithotripter of claim 16, wherein the wave guide shaft has a shaft length that is configured to deliver the ultrasonic waveform at a maximum amplitude of the ultrasonic waveform.

18. The lithotripter of claim 17, wherein the shaft length is provided in an increment of a half ultrasonic wavelength of the ultrasonic waveform.

19. The lithotripter of claim 12, further comprising a pulsater configured to gate the ultrasonic waveform.

20. A lithotripsy system for fragmenting urinary tract stones, the lithotripter comprising:
an ultrasonic driver configured to produce an ultrasonic waveform having an ultrasonic frequency;
a sonic driver configured to produce a sonic waveform having a sonic frequency selected according to a size of a urinary tract stone and about equal to a natural frequency of the urinary tract stone, the sonic driver being coupled to the ultrasonic driver;
a stone size detector for detecting the size of the urinary tract stone, the stone size detector comprising at least one detector selected from a group of detectors consisting of an optical detector and an ultrasonic echo detector, the lithotripter being configured to automatically set at least one of the sonic driver or the ultrasonic driver to produce the sonic or ultrasonic waveform at the selected frequency according to the size of the urinary tract stone; and
a wave guide shaft for transmitting the ultrasonic and sonic waveforms to the urinary tract stone, the wave guide shaft being coupled to at least one of the ultrasonic driver and the sonic driver.

21. The lithotripter of claim 20, wherein the sonic driver is an electromagnetic linear driver, and the ultrasonic driver is a piezoelectric device.

22. The lithotripter of claim 21, wherein the ultrasonic driver and the sonic driver are disposed concentrically, and wherein the sonic driver has portions forming a cavity therein, the ultrasonic driver being disposed in the cavity of the sonic driver.

23. The lithotripter of claim 20, further comprising a driver housing, the ultrasonic driver and the sonic driver being disposed within the driver housing, wherein the ultrasonic driver and the sonic driver are disposed in series within the driver housing, wherein the ultrasonic driver has a proximal end and a distal end, the sonic driver has a proximal end and a distal end, and wherein the proximal end of the ultrasonic driver is disposed adjacent to the distal end of the sonic driver.

24. The lithotripsy system of claim 20, wherein the lithotripter is configured to set the sonic driver to produce the sonic waveform at a first frequency if the urinary tract stone is greater than about 10 millimeters in diameter, a second frequency if the urinary tract stone is greater than about 2 millimeters and less than or equal to about 10 millimeters in diameter, and a third frequency if the urinary tract stone is less than or equal to about 2 millimeters in diameter.

25. The lithotripter of claim 24, wherein the first frequency is in the range of about 0.3-16 Hz, the second frequency is in the range of about 16-70 Hz, and the third frequency is in the range of about 70-200 Hz, and wherein the ultrasonic driver is configured to provide the ultrasonic waveform at an ultrasonic frequency in the range of about 20-30 kHz.

26. The lithotripter of claim 25, further comprising a closed loop feedback circuit configured to determine a preferred ultrasonic frequency that oscillates at a maximum amplitude.

27. The lithotripter of claim 26, further comprising first and second springs.

28. The lithotripter of claim 27, wherein the lithotripter has portions forming a lumen therethrough for at least one of suctioning and irrigating a urinary tract.

* * * * *